US012183464B2

(12) United States Patent
Aronovich et al.

(10) Patent No.: US 12,183,464 B2
(45) Date of Patent: Dec. 31, 2024

(54) PREDICATION OF A HEADACHE

(71) Applicant: Indolex Pharmatech Ltd., Tel Aviv (IL)

(72) Inventors: Eddie Aronovich, Ramat HaSharon (IL); Gad Reshef, Ramat HaSharon (IL); Adar Frenkel, Yavne (IL)

(73) Assignee: Indolex Pharmatech Ltd., Tel Aviv (IL)

( * ) Notice: Subject to any disclaimer, the term of this patent is extended or adjusted under 35 U.S.C. 154(b) by 0 days.

(21) Appl. No.: 17/954,507

(22) Filed: Sep. 28, 2022

(65) Prior Publication Data

US 2024/0105334 A1    Mar. 28, 2024

(51) Int. Cl.
*G16H 50/20*    (2018.01)

(52) U.S. Cl.
CPC .................... *G16H 50/20* (2018.01)

(58) Field of Classification Search
CPC ..................................... G16H 50/20
USPC .............................................. 705/2
See application file for complete search history.

(56) References Cited

U.S. PATENT DOCUMENTS

| 2018/0102187 A1* | 4/2018 | Apte ............. C12Q 1/6883 |
| 2021/0002026 A1 | 1/2021 | Hsu |
| 2021/0142897 A1* | 5/2021 | McLendon ........ G16H 40/63 |

FOREIGN PATENT DOCUMENTS

WO    WO-2014164717 A1 * 10/2014 ............ A61B 5/01

OTHER PUBLICATIONS

De Brouwer, Mathias et al. "mBrain: towards the continuous follow-up and headache classification of primary headache disorder patients." BMC medical informatics and decision making vol. 22,1 87. Mar. 31, 2022, doi:10.1186/s12911-022-01813-w (Year: 2022).*
Gyan, Sonia Nicole; Perception of physical state and environmental stress in chronic headache; University of Cincinnati. ProQuest Dissertations Publishing, 1994. 9520062. (Year: 1994).*
Aguilar-Shea et al. "Migraine Review for General Practice", Atención Primaria, 54(2): 102208-1-102208-8, Published Online Nov. 16, 2021.
Andreou et al. "Mechanisms of Migraine as A Chronic Evolutive Condition", The Journal of Headache and Pain, 20(1): 117-1-117-17, Dec. 23, 2019.
AstraZeneca "The Migraine Disability Assessment Test, MIDAS", AstraZeneca Pharmaceuticals, Innovative Medical Research, 1 P., 2007.

(Continued)

*Primary Examiner* — Hiep V Nguyen
(74) *Attorney, Agent, or Firm* — M&B IP Analysts, LLC

(57) ABSTRACT

There is provided a computer implemented method for predicting a headache for a subject, comprising: feeding a plurality of physiological, behavioral, and environmental parameters obtained from a plurality of sensors monitoring the subject, into a machine learning model, and obtaining the prediction of the headache for the subject as an outcome of the machine learning model, wherein the machine learning model is trained on a training dataset of a plurality of records of a plurality of sample individuals, wherein a record includes a plurality of sample physiological, behavioral, and environmental parameters of a sample individual and a ground truth label indicative of a state of a headache of the sample individual.

23 Claims, 11 Drawing Sheets

(56) References Cited

OTHER PUBLICATIONS

Derry et al. "Paracetamol (Acetaminophen) With or Without An Antiemetic for Acute Migraine Headaches in Adults", The Cochrane Database of Systematic Reviews, 2013(4): CD008040-1-CD008040-49, Published Online Apr. 30, 2013.

Dodick et al. "Consensus Statement: Cardiovascular Safety Profile of Triptans (5-HT1B/1D Agonists) in the Acute Treatment of Migraine", Headache, 44(5): 414-425, Published Online May 7, 2004.

Eigenbrodt et al. "Diagnosis and Management of Migraine in Ten Steps", Nature Reviews Neurology, 17(8): 501-514, Published Online Jun. 18, 2021.

Goadsby et al. "Neurobiology of Migraine", Neuroscience, 161(2): 327-341, Published Online Mar. 19, 2009.

Hawker et al. "Measures of Adult Pain: Visual Analog Scale for Pain (VAS Pain), Numeric Rating Scale for Pain (NRS Pain), McGill Pain Questionnaire (MPQ), Short-Form McGill Pain Questionnaire (SF-MPQ), Chronic Pain Grade Scale (CPGS), Short Form-36 Bodily Pain Scale (SF-36 BPS), and Measure of Intermittent and Constant Osteoarthritis Pain (ICOAP)", Arthritis Care & Research, 63(Suppl.11): S240-S252, Nov. 2011.

Johnston et al. "Triptans for the Management of Migraine", Drugs, 70(12): 1505-1518, Aug. 20, 2010.

Kelman "The Triggers or Precipitants of the Acute Migraine Attack", Cephalalgia, 27(5): 394-402, Published Online Mar. 30, 2007.

Kesserwani "Migraine Triggers: An Overview of the Pharmacology, Biochemistry, Atmospherics, and Their Effects on Neural Networks", Cureus, 13(4): e14243-1-e14243-9, Apr. 1, 2021.

Kipple "Resources: The KIP Scale", CHSG, The Cluster Headache Support Group, 3 P., Mar. 14, 2017.

Lipton et al. "Migraine Headache: Diagnosis and Current and Emerging Preventive Treatments", The Primary Care Companion for CNS Disorders, 20(Suppl.E1): li1705sulc-1-li1705sulc-8, Dec. 27, 2018.

Marmura et al. "The Acute Treatment of Migraine in Adults: The American Headache Society Evidence Assessment of Migraine Pharmacotherapies", Headache, 55(1): 3-20, Jan. 2015.

Matsangidou et al. "Machine Learning in Pain Medicine: An Up-To-Date Systematic Review", Pain and Therapy, 10(2): 1067-1084, Published Online Sep. 26, 2021.

Rendas-Baum et al. "The Psychometric Properties of the Migraine-Specific Quality of Life Questionnaire Version 2.1 (MSQ) in Chronic Migraine Patients", The Quality of Life Research, 22(5): 1123-1133, Published Online Jul. 15, 2012.

Shin et al. "Headache Impact Test-6 (HIT-6) Scores for Migraine Patients: Their Relation to Disability as Measured From A Headache Diary", Journal of Clinical Neurology, 4(4): 158-163, Published Online Dec. 31, 2008.

Silberstein et al. "Preventive Migraine Treatment", Continuum, 21(4 Headache): 973-989, Aug. 2015.

Stewart et al. "Validity of the Migraine Disability Assessment (MIDAS) Score in Comparison to A Diary-Based Measure in A Population Sample of Migraine Sufferers", Pain, 88(1): 41-52, Oct. 2000.

Stovner et al. "The Global Prevalence of Headache: An Update, With Analysis of the Influences of Methodological Factors on Prevalence Estimates", The Journal of Headache and Pain, 23(1): 34-1-34-17, Published Online Apr. 12, 2022.

Zhang et al. "Reinforcement Learning in Clinical Medicine: A Method to Optimize Dynamic Treatment Regime Over Time", Annals of Translational Medicine, 7(14): 345-1-345-10, Jul. 2019.

International Search Report for PCT/IB2023/059419, dated Jan. 31, 2024. Searching Authority Israel Patent Office, Jerusalem, Israel.

Stubberud, Anker, et al. "Forecasting migraine with machine learning based on mobile phone diary and wearable data." Cephalalgia 43.5 (2023): 03331024231169244 Stubberud, Anker, et al. Oct. 25, 2023 (Oct. 25, 2023) the whole document.

Written Opinion of the Searching Authority for PCT/IB2023/059419, dated Jan. 31, 2024. Searching Authority Israel Patent Office, Jerusalem, Israel.

\* cited by examiner

PREDICATION OF A HEADACHE

FIELD AND BACKGROUND OF THE INVENTION

The present invention, in some embodiments thereof, relates to medical treatments and, more specifically, but not exclusively, to systems and methods for treatment and/or management of headaches.

Migraine is one of the most ubiquitous syndromes that influences approximately 14% of the population at working age. Nevertheless, there is no optimal treatment for migraines. Migraine is a recurrent and episodic disease that currently has no cure and that in general allows an adequate quality of life when it is known and treated. Inadequate treatment of migraine attack has a huge socio-economic impact and also increases the risk of transformation of migraine into its chronic forms.

SUMMARY OF THE INVENTION

According to a first aspect, a computer implemented method for predicting a headache for a subject, comprises: feeding a plurality of physiological, behavioral, and environmental parameters obtained from a plurality of sensors monitoring the subject, into a machine learning model, and obtaining the prediction of the headache for the subject as an outcome of the machine learning model, wherein the machine learning model is trained on a training dataset of a plurality of records of a plurality of sample individuals, wherein a record includes a plurality of sample physiological, behavioral, and environmental parameters of a sample individual and a ground truth label indicative of a state of a headache of the sample individual.

According to a second aspect, a computer implemented method for training a machine learning model for predicting a headache for a subject, comprises: creating a training dataset of a plurality of records of a plurality of sample individuals, wherein a record includes a plurality of sample physiological, behavioral, and environmental parameters of a sample individual and a ground truth label indicative of a state of a headache of the sample individual, and training a machine learning model on the training dataset, wherein the prediction of the headache for the subject is obtained as an outcome of the machine learning model in response to an input of a plurality of physiological, behavioral, and environmental parameters obtained from a plurality of sensors monitoring the subject.

According to a third aspect, a system for predicting a headache for a subject, comprises: at least one processor executing a code for: feeding a plurality of physiological, behavioral, and environmental parameters obtained from a plurality of sensors monitoring the subject, into a machine learning model, and obtaining the prediction of the headache for the subject as an outcome of the machine learning model, wherein the machine learning model is trained on a training dataset of a plurality of records of a plurality of sample individuals, wherein a record includes a plurality of sample physiological, behavioral, and environmental parameters of a sample individual and a ground truth label indicative of a state of a headache of the sample individual.

According to a fourth aspect, a computer implemented method for predicting a headache for a subject, comprises: feeding a plurality of physiological, behavioral, and environmental parameters obtained from a plurality of sensors monitoring the subject, into a machine learning model, and obtaining the prediction of the headache for the subject as an outcome of the machine learning model, wherein the machine learning model is further trained on a personalized training dataset of a plurality of personalized records of the subject, wherein a personalized record includes a plurality of historical physiological, behavioral, and environmental parameters of the subject and a ground truth label indicative of the state of the headache of the subject.

In a further implementation form of the first, second, third, and fourth aspects, the plurality of physiological, behavioral, and environmental parameters are a combination of one or more of the following: sum of calories burned, mean heart rate variability, maximum heart rate, sleep recover score, number of steps, movement during the night of the subject, peak and/or minimum oxygen saturation, changes in heart rate during the night, sleeping segment length, mean ambient temperature, and median barometric pressure.

In a further implementation form of the first, second, third, and fourth aspects, the plurality of physiological parameters are selected from a group consisting of: movement during the night, $SPO_2$ peaks, changes in heart rate during the night, and sleeping segment lengths indicating how long the user slept each time between waking events.

In a further implementation form of the first, second, third, and fourth aspects, at least one of the plurality of physiological, behavioral, and environmental parameters fed into the machine learning model comprises a time sequence of a plurality of measurements obtained over a time interval.

In a further implementation form of the first, second, third, and fourth aspects, the headache is selected from a group comprising migraine and cluster headache.

In a further implementation form of the first, second, third, and fourth aspects, further comprising: in response to the prediction of the headache, treating the subject for the headache by administering a treatment effective for the headache.

In a further implementation form of the first, second, third, and fourth aspects, treatment effective for the headache is selected from a group comprising: NSAID (non-steroidal anti-inflammatory), acetaminophen, aspirin, triptans, etoprolol, propranolol, amitriptyline, divalproex, topiramate, or erenumab-aooe, tricyclic antidepressants, cognitive behavior therapy, biofeedback, massage, acupuncture, exercise, sleep therapy, stress reduction therapy, and change in diet.

In a further implementation form of the first, second, third, and fourth aspects, the prediction of the headache comprises a plurality of scores of a plurality of fields of a standardized evaluation tool indicative of pain and/or disability due to the headache, wherein the record includes ground truth labels indicative of sample scores for the plurality of fields of the standardized evaluation tool.

In a further implementation form of the first, second, third, and fourth aspects, the plurality of physiological parameters obtained from the plurality of sensors are selected from a group comprising: location of the subject obtained from a location sensor, motion of the subject obtained from a motion sensor, heart rate or HRV obtained from a heart rate sensor, $SPO_2$ level obtained from an sensor that measures $SPO_2$ level, respiration rate obtained from a respiration rate sensor, electro dermal activity obtained from an electrode sensor, activity data obtained from an activity sensor, sleep data obtained from a sleep sensor, or computed metrics returned by the sensor including sleeping metrics, and sleep recovery.

In a further implementation form of the first, second, third, and fourth aspects, the indication of the state of the headache is obtained by a manual user input into a user interface of a mobile device, the manual user input indicative of at least one of: when headache started, when headache ended, pain level of the headache, disability caused by headache, and treatment taken by the subject.

In a further implementation form of the first, second, third, and fourth aspects, the behavioral parameters are selected from a group comprising: attendance, involvement, social meetings, exercise, hobbies, sending messages, and talking on a phone.

In a further implementation form of the first, second, third, and fourth aspects, the environmental parameters and at least one environmental sensor from which the environmental parameters are defined is selected from a group comprising: temperature obtained from a thermometer, pressure obtained from a pressure sensor, light intensity obtained from a light intensity sensor, noise intensity obtained from a noise intensity sensor, and fetched from other data resources.

In a further implementation form of the first, second, third, and fourth aspects, the prediction of the headache comprises prediction of onset of the headache when the subject does not have the headache at a time interval during which the plurality of physiological parameters are obtained.

In a further implementation form of the first, second, third, and fourth aspects, further comprising: synchronizing the plurality of physiological, behavioral and environmental parameters, wherein the synchronized plurality of physiological, behavioral and environmental parameters are fed into the machine learning model, wherein the record includes a plurality of synchronized sample physiological, behavioral and environmental parameters.

In a further implementation form of the first, second, third, and fourth aspects, the training dataset includes records of the subject and excludes records of other subjects for training a personalized machine learning model for the subject.

In a further implementation form of the first, second, third, and fourth aspects, further comprising dynamically updating the machine learning model by dynamically creating a new record using new values of the plurality of physiological, behavioral and environmental parameters and a new value for the ground truth label.

In a further implementation form of the first, second, third, and fourth aspects, further comprising feeding an indication of administered treatment into the machine learning model in combination with the plurality of physiological, behavioral and environmental parameters, wherein the prediction of the headache includes a prediction of an adaptation of the treatment for preventing onset of the headache when the subject is not currently experiencing a headache or for reduction of severity of the headache currently experienced by the subject, wherein the record further includes an indication of treatment administered to the sample individual and the ground truth further includes an indication of an adaptation of the treatment.

In a further implementation form of the first, second, third, and fourth aspects, the adaptation of the treatment includes at least one of: a recommendation to replace approved drugs and/or drug combinations between treatments, effectiveness of medication, a change in dose of the medication, a change in frequency of administration of the medication, physical activity, change in nutrition and/or diet, wherein the adaptation is for at least one of: likely to further reduce intensity of pain in comparison to a current treatment, and likely to reduce side effects in comparison to the current treatment.

In a further implementation form of the first, second, third, and fourth aspects, further comprising treating the subject by administration of the adaptation of the treatment.

In a further implementation form of the first, second, third, and fourth aspects, when the subject is currently experiencing a headache, the plurality of physiological, behavioral and environmental parameters includes an indication of the severity and disability of pain due to the headache, obtained by at least one of: entered by the subject via a user interface, and computed from other physiological parameters, wherein the adaptation of the treatment is for reducing the severity of the pain or prevention of the pain.

In a further implementation form of the first, second, third, and fourth aspects, when the subject is currently experiencing a headache, further comprising: feeding a subset of the plurality of physiological parameters into a pain machine learning model, obtaining an indication of the severity of pain of the headache as an outcome of the pain machine learning model, wherein the pain machine learning model is trained on a pain training dataset of a plurality of pain records, wherein a pain record includes a sample subset of plurality of physiological, behavioral and environmental parameters of a sample individual and/or of the subject and a ground truth label indicating pain, wherein the indication of the severity of pain is fed into the machine learning model, wherein the prediction of the headache comprises instructions for treatment for preventing of pain or reducing severity of pain of the current headache.

In a further implementation form of the first, second, third, and fourth aspects, when the subject is not currently experiencing a headache, further comprising: feeding a subset of the plurality of physiological parameters into a pain machine learning model, obtaining an indication of predicted a severity of pain for a predicted headache as an outcome of the pain machine learning model, wherein the pain machine learning model is trained on a pain training dataset of a plurality of records, wherein a pain record includes a sample subsets of plurality of physiological parameters of a sample subject and a ground truth label indicating pain, wherein the indication of severity of pain is fed into the machine learning model, wherein the prediction of the headache comprises instructions for treatment for reducing severity of predicted pain of the predicted headache.

In a further implementation form of the first, second, third, and fourth aspects, the machine learning model is implemented based on a reinforcement learning approach, where an action taken by the subject is the administration of a targeted treatment for a current state of the headache, a next state is the prediction of the headache in response to the administered treatment, and a reward is a decrease in pain of the headache, frequency or preventing the headache.

In a further implementation form of the first, second, third, and fourth aspects, further comprising applying a machine learning model interpretability process for computing relative contribution of the parameters towards the outcome generated by the machine learning model representing a specific headache event, selecting at least one most contributing parameter indicative as a trigger for the specific headache event, wherein the selected at least one most contributing parameter is adapted for reducing pain intensity of the specific headache event or avoiding onset of the pain headache event.

In a further implementation form of the first, second, third, and fourth aspects, further comprising extracting a plurality of features from output of the plurality of sensors, the plurality of features comprising the plurality of physiological, behavioral and environmental parameters that are fed into the machine learning model, wherein the record includes a plurality of sample features comprising the sample physiological, behavioral and environmental parameters extracted from the plurality of sensors monitoring the plurality of sample individuals.

In a further implementation form of the first, second, third, and fourth aspects, the training dataset includes excludes records of other subjects for training a personalized machine learning model for the subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
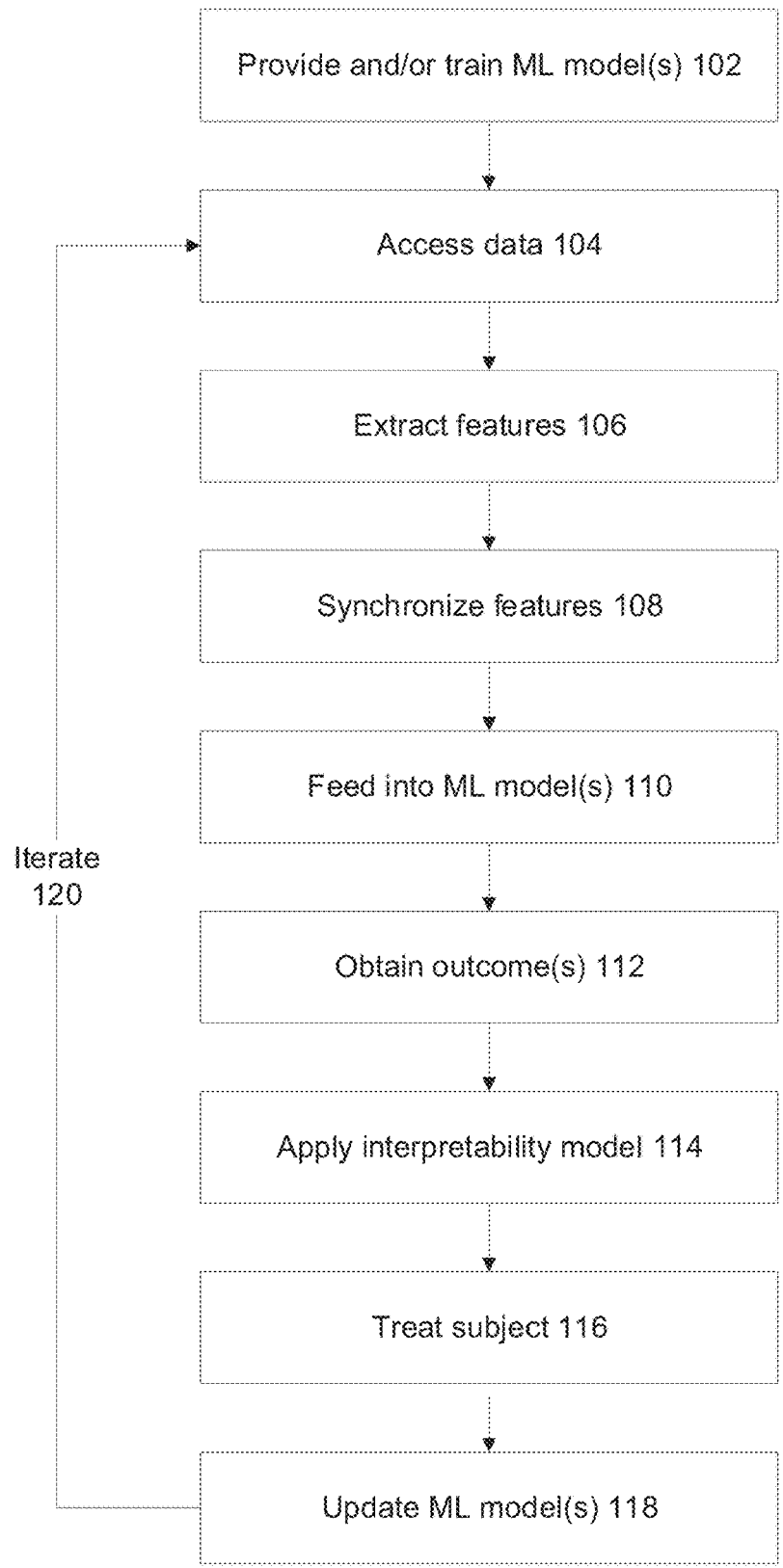
FIG. 1 is a flowchart of a method of predicting a headache for a subject by a trained machine learning model, in accordance with some embodiments of the present invention.

The present invention, in some embodiments thereof, relates to medical treatments and, more specifically, but not exclusively, to systems and methods for treatment and/or management of headaches.

As used herein, the term parameters refers to one or more, optionally all of the following: physiological, behavioral, and environmental parameters. The term parameter may be interchanged with the term features, computed features, or extracted features.

An aspect of some embodiments of the present invention relates to systems, methods, computing devices, and/or code instructions (stored on a data storage device and executable by one or more processors) for predicting a headache of a subject, optionally prior to onset of the headache. The prediction may be for a specific headache event of the subject. Predictions may be performed for each specific headache event. The headache may be a migraine and/or cluster headache. Multiple parameters are obtained from data outputted by sensors monitoring a subject. The parameters, which may include physiological, and/or behavioral, and/or environmental parameters, are fed into a machine learning (ML) model. The ML model is trained on a training dataset of multiple records, obtained from sample individuals and/or from the subject. A record includes sample parameters of the sample individual and/or the subject, and a ground truth indicating a state of a headache of the sample individual and/or the subject. The training dataset may be personalized for the subject, including historical parameters of the subject and excluding parameters of other subjects. A prediction of the headache for the subject, optionally prior to onset of the headache, is obtained as an outcome of the ML model. The subject may be treated according to the prediction, for reducing pain of the headache or preventing onset of the headache.

Inventors discovered that certain parameters when fed into the ML model generate an outcome of a prediction of headaches in subjects. Such parameters have not been previously used to predict headaches. The discovered parameters include one or more (e.g., combination) of: sum of calories burned, heart rate variability metric (e.g., mean), heart rate metric (e.g., max), sleep recover score, number of steps, movement during the night of the subject (e.g., steps), oxygen saturation ($SPO_2$) metrics (e.g., $SPO_2$ peaks, and/or minimum) changes in heart rate during the night, sleeping segment length (in contrast to total sleeping time), mean ambient temperature, and median barometric pressure. These parameters may serve as bio-markers for prediction of headaches, and/or for reduction and/or avoidance of headaches by adaptation of the parameters and/or early administration of treatment, as described herein. In the state of the art, there are no known bio-markers that are proven to be linked to migraines. Noise and food are believed to trigger migraines in general. Inventors discovered that parameters may be used to predict specific headache events, as described herein in additional detail.

An aspect of some embodiments of the present invention relates to systems, methods, computing devices, and/or code instructions (stored on a data storage device and executable by one or more processors) for training a ML model for predicting a headache of a subject, optionally prior to onset of the headache. The headache may be a migraine and/or cluster headache. A training dataset of multiple records is created. A record includes sample parameters of each one of multiple sample individuals and/or sample parameters of the subject, and a ground truth indicating a state of a headache of the sample individual and/or the subject. The parameters may include physiological, and/or behavioral, and/or environmental parameters. The training dataset may be personalized for the subject, including historical parameters of the subject and excluding parameters of other subjects. The ML model is trained on the training dataset. The prediction of the headache for the subject is obtained as an outcome of the ML model in response to an input of physiological parameters obtained from a plurality of sensors monitoring the subject.

At least some implementations described herein address the technical problem of assessment of pain of a headache, in particular, migraine and/or cluster headache. Pain assessment is used, for example, for guiding treatment and/or evaluation of disability due to the headache. For example, strong opioids may be prescribed for severe pain, and weak analgesics may be taken for mild pain. In another example, subjects with severe migraines may qualify for certain medical benefits and/or other benefits such as qualifying to use sick days from work.

It is noted that migraines and/or cluster headaches are chronic medical condition, that is repeatedly experienced by the subject. When left untreated, the migraine and/or cluster headaches may represent a form of disability, such as when subjects cannot continue working and/or otherwise function normally in performing activities of daily living. Migraines and/or cluster headaches are different from other headaches, which may be triggered by other causes and/or may be one-time events, such as headaches due to stroke, headaches due to stress, headaches due to sinus problems, headaches due to infection, headaches due to dehydration, and the like.

At least some implementations described herein improve upon existing approaches for assessing pain of headaches, which are problematic. Existing approaches are based on reports provided by the subject, such as from 1-10, or reported disability experienced due to the pain. Pain assessment of headaches is biased. Pain is subjective and the subject cannot estimate pain levels well when thinking about historically experienced pain. Pain assessment is partial. The impact of pain can be measured and compared to a regular notebook. Comparing pain scores between different epochs is challenging and measurable pain metrics can be used for treatment personalization, drug discovery and better understanding of illness. There are tools available for estimating pain and/or disability, for example, MIDAS (Migraine Disability Assessment), VAS (Visual Analog Scale for Pain), KIP Scale (for describing pain of a cluster headache attack), and the like. However, such tools require manual evaluation by the subject.

At least some implementations described herein improve the technical field of medical treatment, by providing approaches for reducing and/or preventing pain due to headaches. At least some implementations described herein improve the technical field of machine learning, by providing machine learning models for objectively and/or repeatedly assessing pain and/or disability due to headaches, optionally using existing scales.

At least some implementations described herein provide an objective pain index based on disability consequences of migraine attacks, which is related to known subjective scales used as best practice: HIT-6 and MIDAS. Optionally, at least some implementations described herein provide adaptive treatment adjustments based on reinforcement learning methods using the ability to identify pain and measure it's consequences as a feedback loop.

In at least some implementation, the solution to the technical problem, and/or the improvement over existing approaches, and/or improvement to the field, is based on mapping data obtained from sensors to fields of developed pain assessment tools, which provides an objective and/or repeatable approach for using the pain assessment tools.

At least some implementations described herein address the technical problem of predicting future onset of headache. Headache attacks such as migraine and/or cluster headache attacks, start without any notice, and cannot be predicted using known approaches. Although there is a belief that noise and food are somehow correlated with migraine attacks in general, specific attacks cannot be predicted. There are no known bio-markers that are proven to cause migraines. Taking preventive medication before an attack starts is believed by physicians to be more effective than afterwards, however, taking the preventing medical is difficult since predicting the headache attacks is difficult.

At least some implementations described herein improve upon existing approaches for treating headaches, by predicting future onset of headaches, before the headache has started. Specific headache attacks may be predicted, optionally during a predicted future time interval. Prediction of specific future headache events enables administering treatment for the future headache before the headache has started, which is expected to reduce or prevent the pain from the headache, and may prevent the attack altogether.

At least some implementations described herein improve the technical field of medical treatment, by predicting future headaches and administering treatment for the future headache before the headache has started, which is expected to reduce or prevent the pain from the headache, and may prevent the attack altogether. At least some implementations described herein improve the technical field of machine learning, by providing machine learning models for predicting future onset of headaches.

In at least some implementation, the solution to the technical problem, and/or the improvement over existing approaches, and/or improvement to the field, is based on ML models for predicting future headaches.

At least some implementations described herein address the technical problem of selecting the best treatment for reducing the pain of a headache. There are various pharmacological nonspecific acute treatments, specific acute treatments, and prophylactic treatments, for headaches. Medication dosage and frequency given to patients are based on general guidelines and are not optimized to specific patients. For pharmacological treatments, dosage and frequency are usually set by general body parameters like sex, weight and age. In some cases it causes adverse effects and in some other cases, the treatment is not helpful. Moreover, since existing approaches for optimization of medications are based on self-reports by patients, and pain is subjectively measured, it is hard to optimize the treatment and to show efficacy of treatment.

At least some implementations described herein improve upon existing approaches for selecting the best treatment for reducing the pain of a headache. The best treatment may include one or more of: which medication is most likely to have the strongest effect in reducing the intensity of pain when to take the medication, dosage of the medication, frequency of administration of the medication, and medication most likely to have the lowest side effects.

At least some implementations described herein improve the technical field of medical treatment, by selecting the best treatment for reducing the pain of a headache. At least some implementations described herein improve the technical field of machine learning, by providing machine learning models for selecting the best treatment for reducing the pain of a headache.

In at least some implementation, the solution to the technical problem, and/or the improvement over existing approaches, and/or improvement to the field, is based on ML models that recommend adaptations for currently administered treatments for reducing the intensity of pain due to headache.

At least some implementations described herein address the technical problem of identifying triggers of headaches, in particular, migraine. The cause of migraine attacks is not known, but there is evidence that migraine-associated triggers are common and may fall into five main categories: emotional stress, menstrual-induced, sleep disturbance, food and alcoholic beverages, and weather changes. As described herein, Inventors discovered additional triggers that were previously known, for example, physical activity, cardiovascular metrics, and respiratory metrics. Upon knowing the trigger, a subject can either abstain from the trigger if possible and in case of triggers that are unavoidable, the subject can prepare herself. Knowing the triggers allows the subject to manage the attacks and get medical assistance in cases it is plausible.

At least some implementations described herein improve upon existing approaches for detecting triggers for migraines, optionally detecting specific custom triggers for users for specific headache events. There may be different triggers that are detected for different predicted headache events. Identifying the specific triggers may enable taking action to prevent the onset of the specific headache event for the specific user. Using known approaches, migraine triggers are hard to detect. Existing approaches use detailed diaries of attacks (also called headache calendars) and questionnaires. However, the probable cause of the migraine is not easy to track. In existing approaches, patients are generally questioned for possible known triggers, and general recommendations for lifestyle changes are made to patients. At best, general triggers that may trigger migraines, in general, are identified. However, such triggers, such as noise and/or food, are difficult to control. Specific headaches cannot be prevented using known approaches. Knowing the causes of migraine attacks can assist the medics to give the right medication At least some implementations described herein improve the technical field of discovering migraine triggers.

In at least some implementation, the solution to the technical problem, and/or the improvement over existing approaches, and/or improvement to the field, is based on using machine learning interpretability approaches to discover features with the highest correlation with the predicted likelihood of migraine by a machine learning model. The features may be non-traditional features, which have not been previously known to trigger migraines. The features discovered to trigger migraine are customized to each patient, i.e., some triggers are significant in some patients but non-significant in others.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer-readable storage medium (or media) having computer-readable program instructions thereon for causing a processor to carry out aspects of the present invention.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
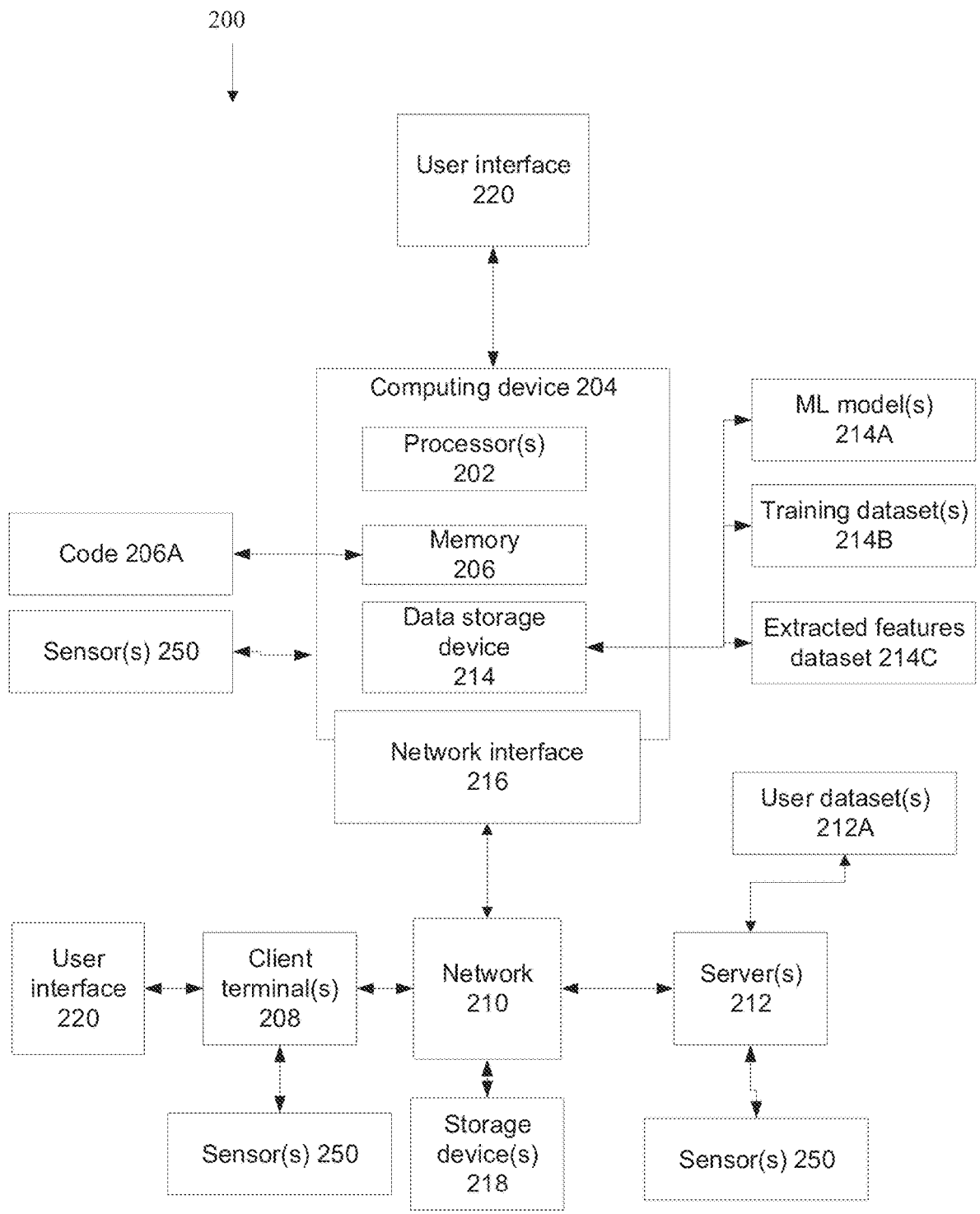
FIG. 2 is a block diagram of components of a system for predicting a headache for a subject by a trained machine learning model and/or for training the machine learning model, in accordance with some embodiments of the present invention.
Figure 3:
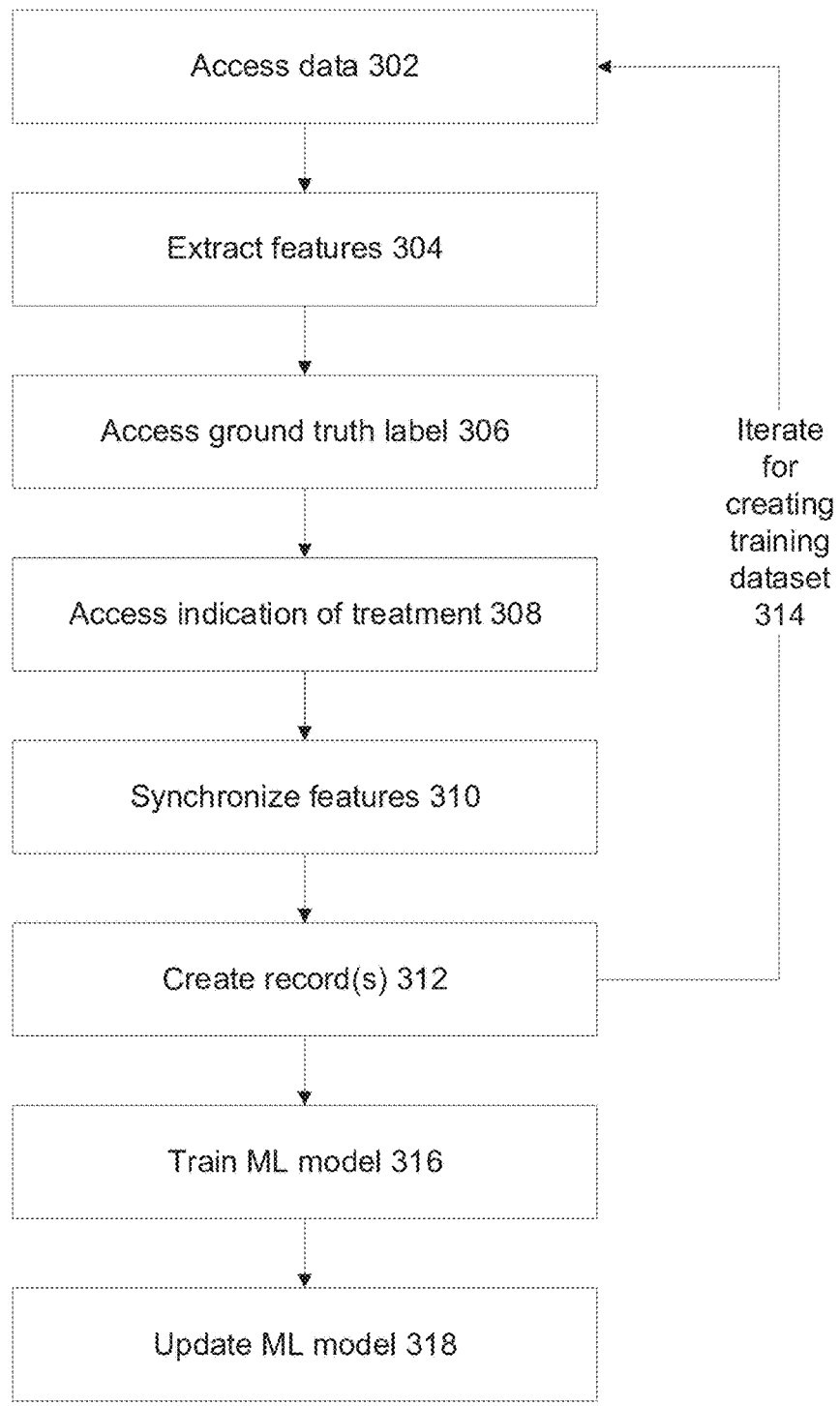
FIG. 3 is a flowchart of a method of training a machine learning model for predicting a headache of a subject, in accordance with some embodiments of the present invention.
Figure 4:
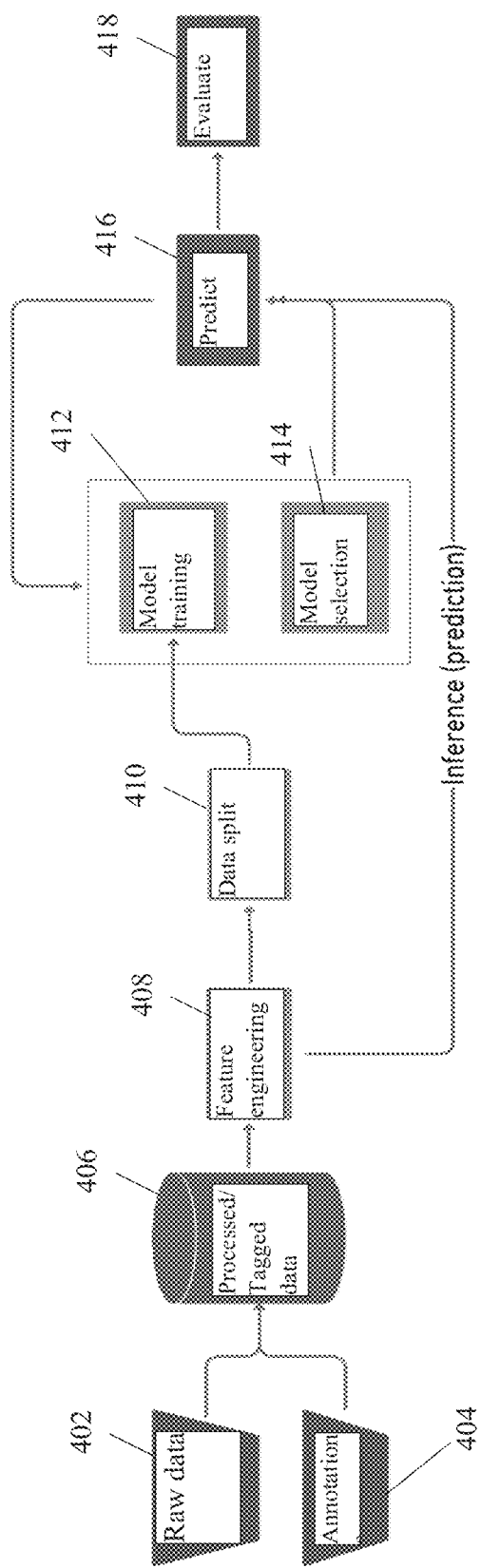
FIG. 4 is a dataflow diagram depicting an exemplary dataflow for creating a machine learning model that predicts headaches, in accordance with some embodiments of the present invention.
Figure 5:
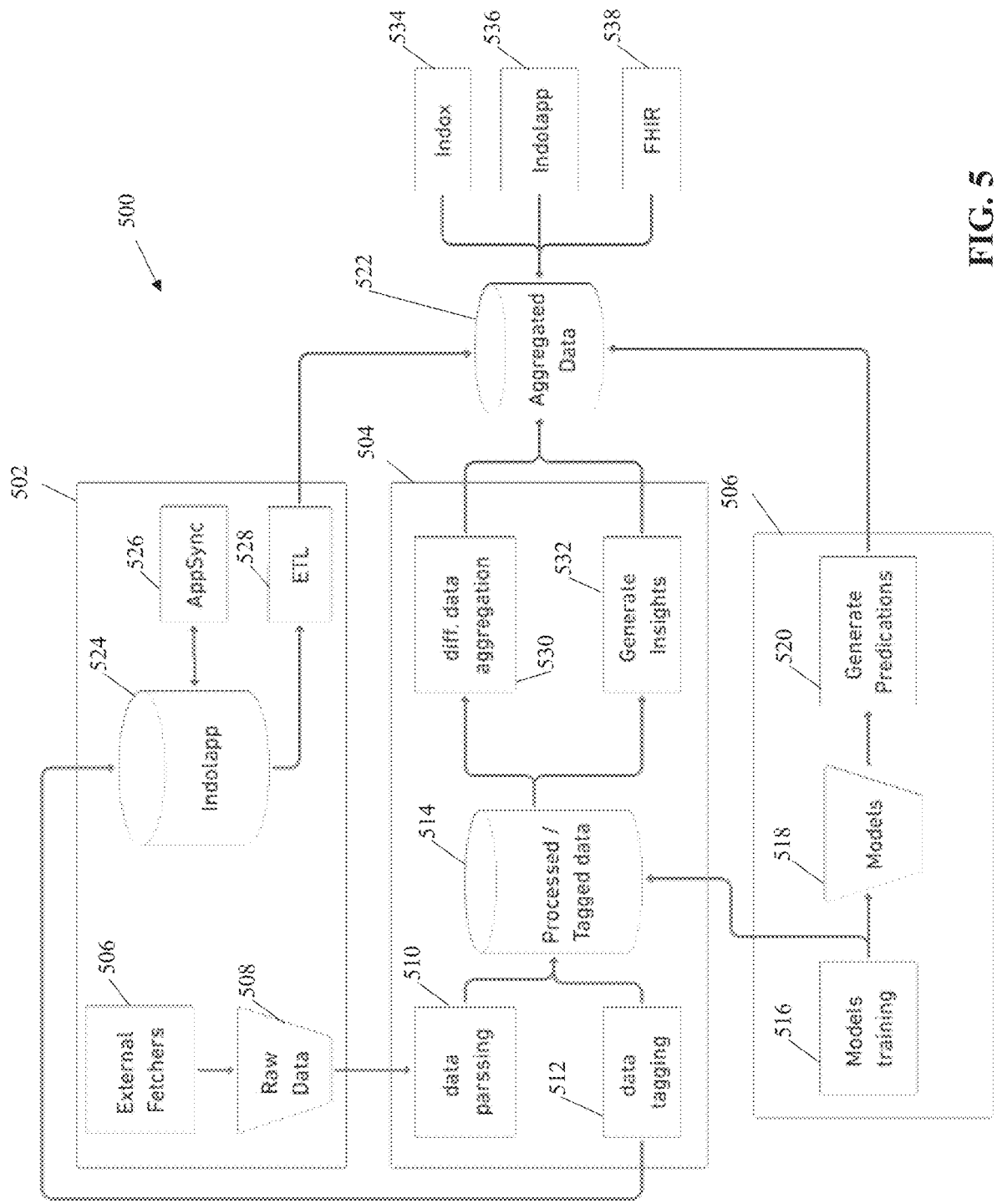
FIG. 5 is a schematic depicting an exemplary architecture for predicting a headache for a subject by a trained machine learning model, in accordance with some embodiments of the present invention.
Figure 6:
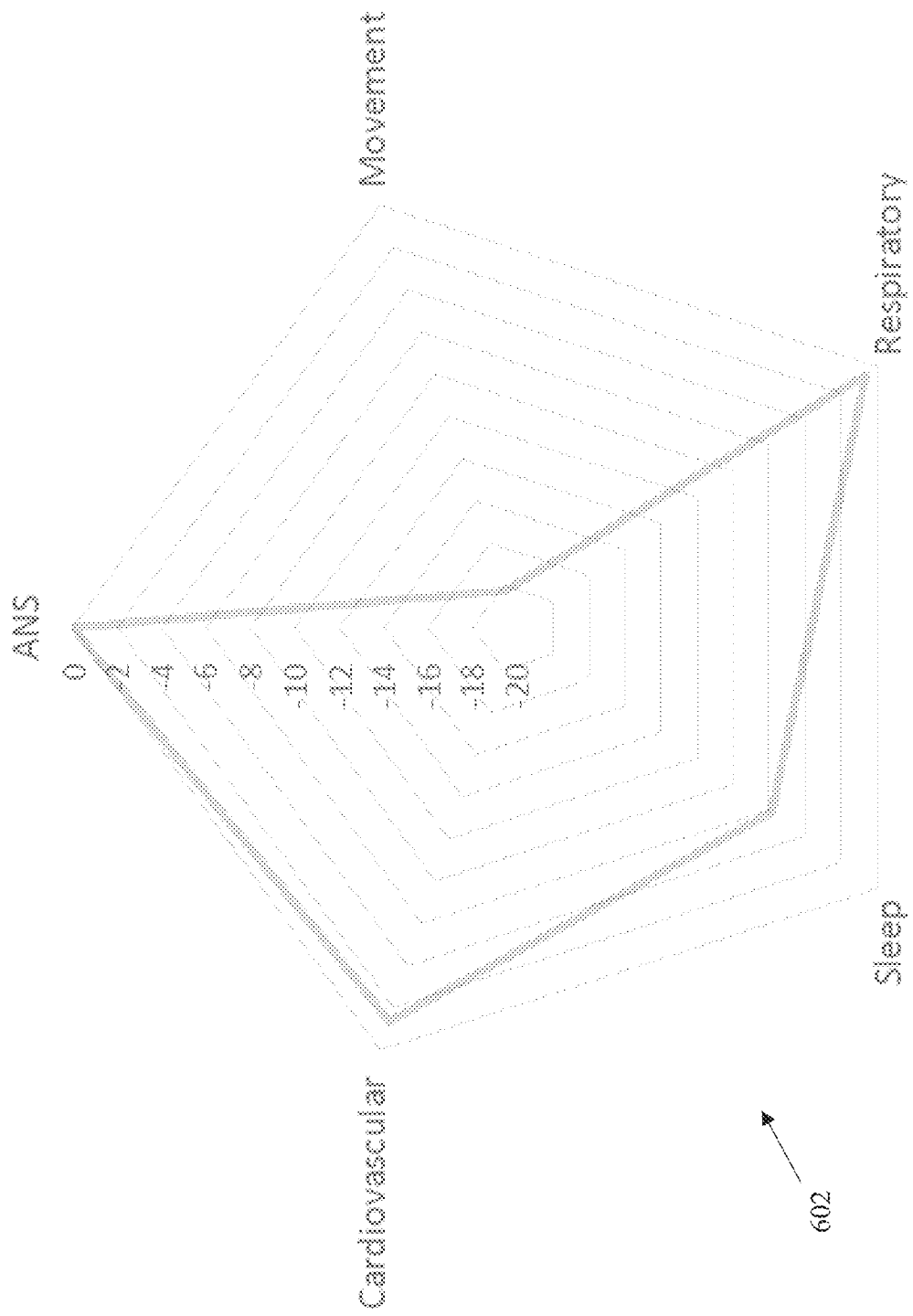
FIG. 6 is a plot of personalized physiological metrics indicating normalized personalized risk factors for a headache for a subject based on the machine learning model, in accordance with some embodiments of the present invention.
Figure 7:
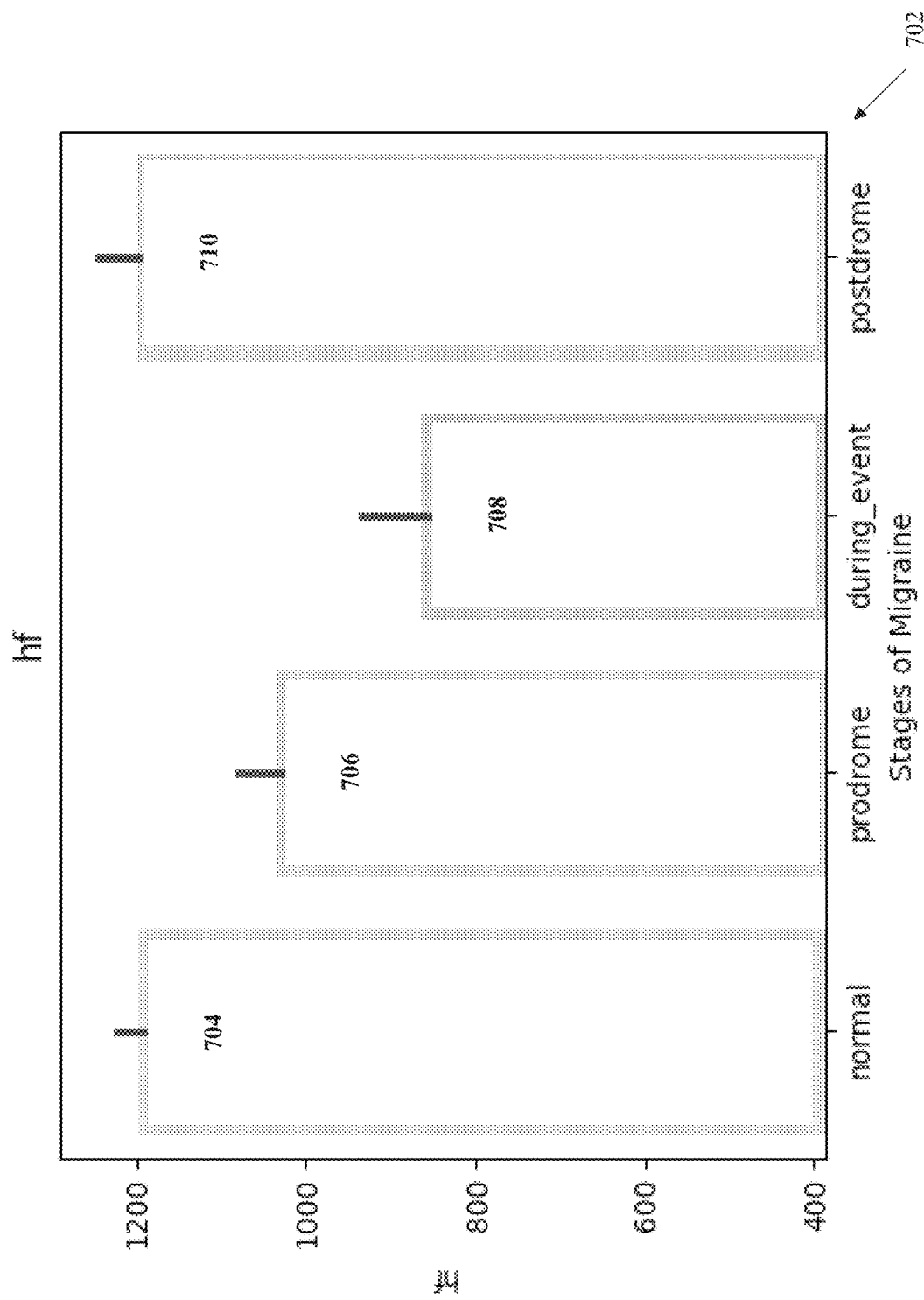
FIG. 7 is a graph indicating stages of migraine as manifested by a user, in accordance with some embodiments of the present invention.
Figure 8:
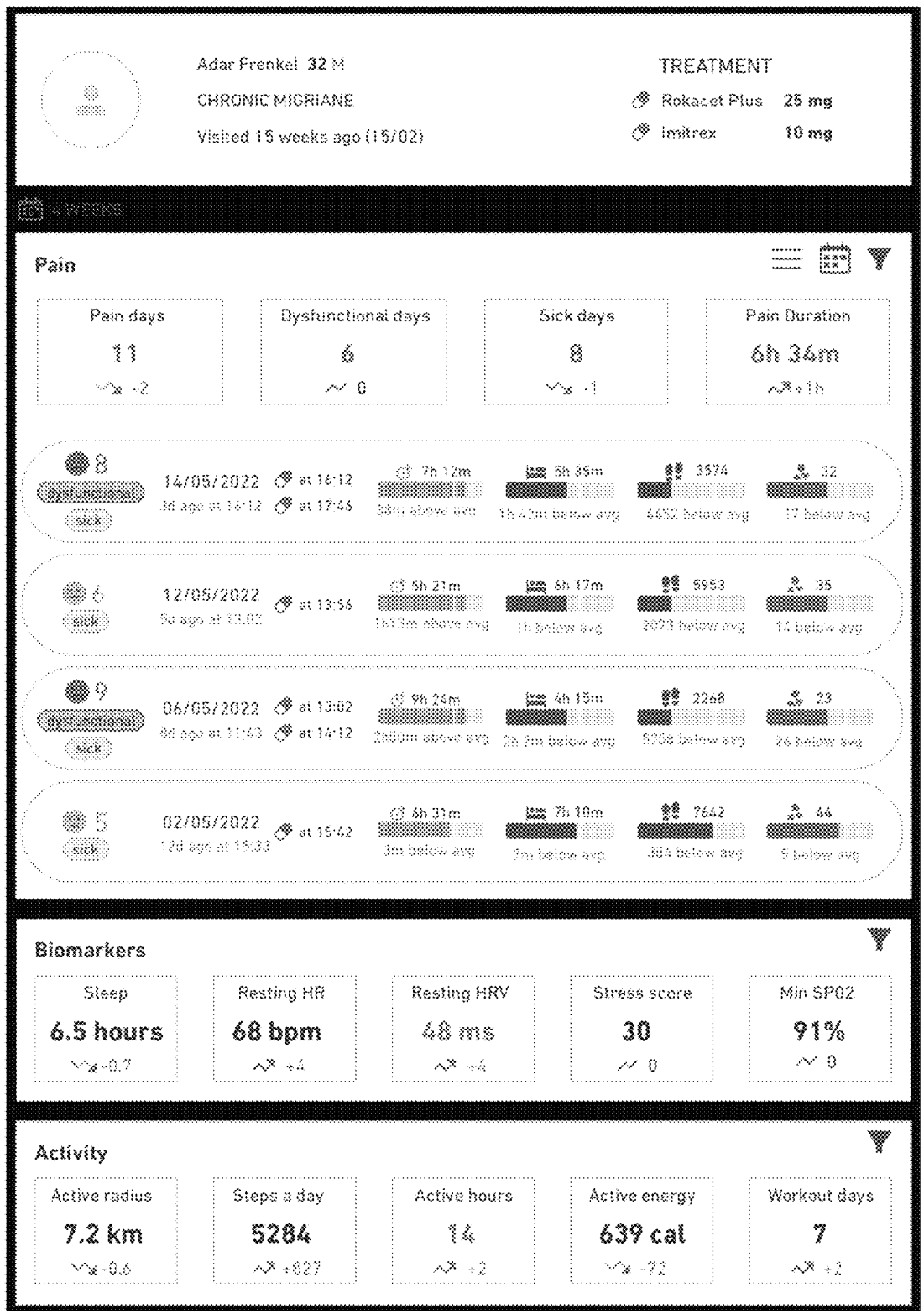
FIG. 8 is a schematic of an exemplary dashboard for monitoring headaches in a subject, in accordance with some embodiments of the present invention.
Figure 9:
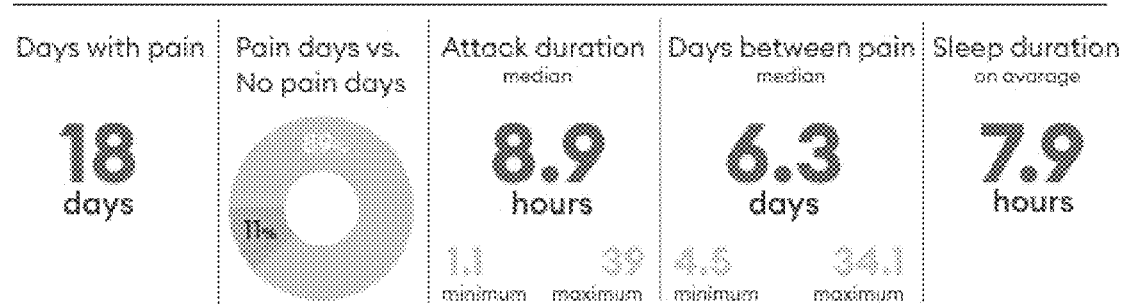
FIG. 9 is a schematic of an exemplary report summarizing headaches, in accordance with some embodiments of the present invention.
Figure 10:
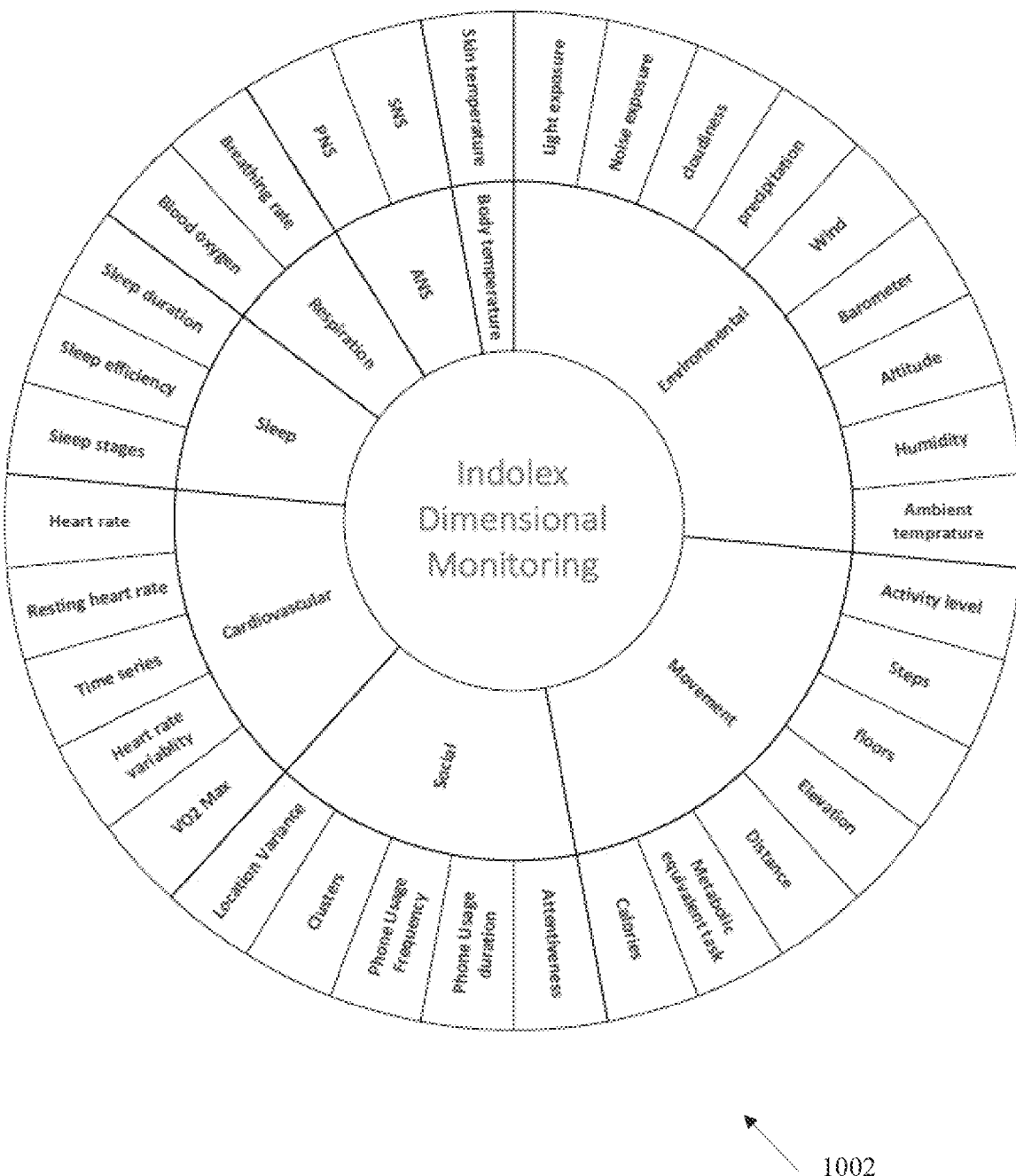
FIG. 10 is a schematic presenting parameters and/or features for predicting a headache, organized into categories, in accordance with some embodiments of the present invention.
Figure 11:
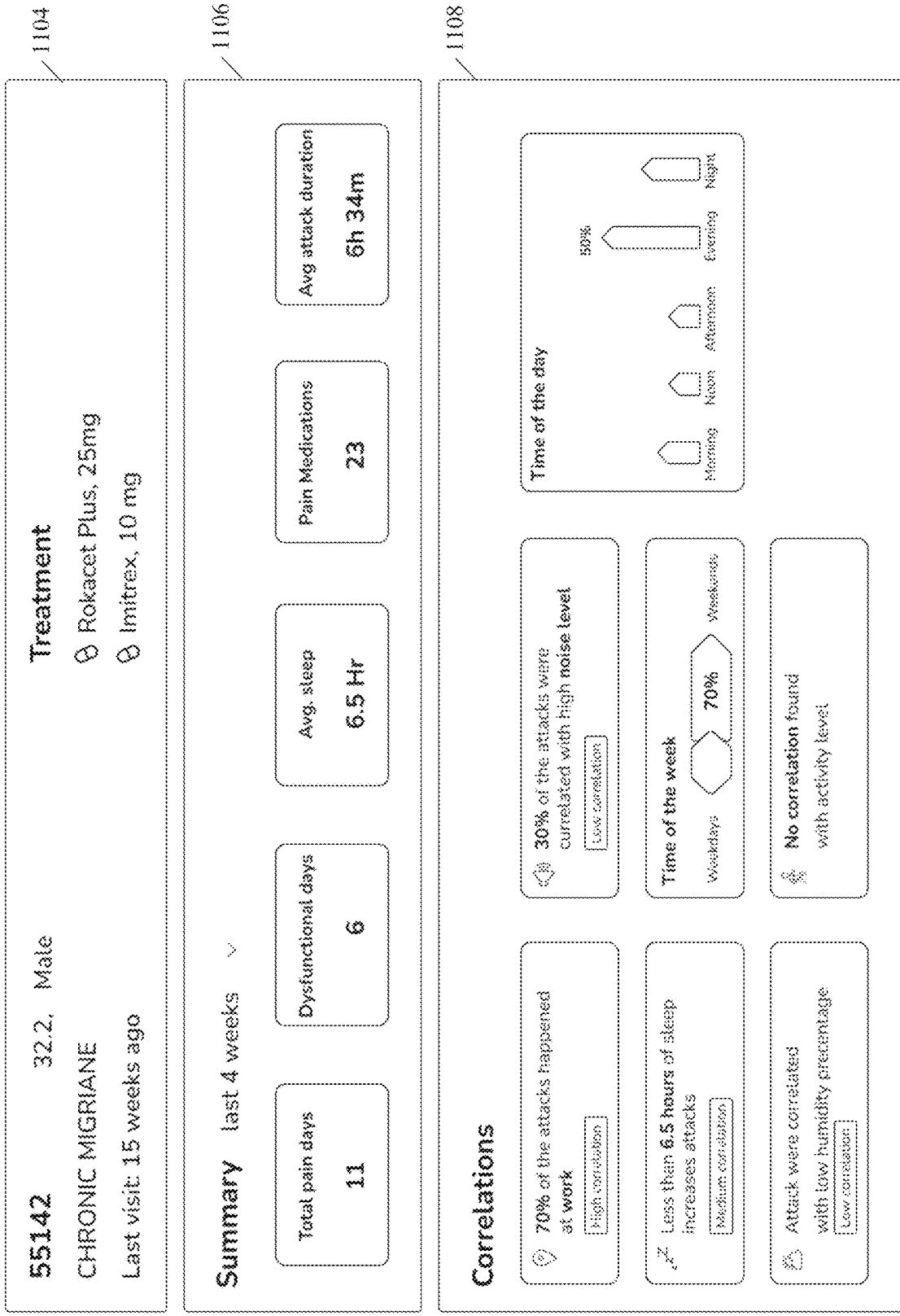
FIG. 11 is a schematic of an exemplary dashboard for presenting parameters correlated with a headache of a user, in accordance with some embodiments of the present invention.

Reference is now made to FIG. 1, which is a flowchart of a method of predicting a headache for a subject by a trained machine learning model, in accordance with some embodiments of the present invention. Reference is also made to FIG. 2, which is a block diagram of components of a system 200 for predicting a headache for a subject by a trained machine learning model and/or for training the machine learning model, in accordance with some embodiments of the present invention. Reference is also made to FIG. 3, which is a flowchart of a method of training a machine learning model for predicting a headache of a subject, in accordance with some embodiments of the present invention. Reference is also made to FIG. 4, which is a dataflow diagram depicting an exemplary dataflow for creating a machine learning model that predicts headaches, in accordance with some embodiments of the present invention. Reference is also made to FIG. 5, which is a schematic depicting an exemplary architecture 500 for predicting a headache for a subject by a trained machine learning model, in accordance with some embodiments of the present invention. Reference is also made to FIG. 6, which is a plot 602 of personalized physiological metrics indicating normalized personalized risk factors for a headache for a subject based on the machine learning model, in accordance with some embodiments of the present invention. Reference is also made to FIG. 7, which is a graph 702 indicating stages of migraine as manifested by a user, in accordance with some embodiments of the present invention. Reference is also made to FIG. 8, which is a schematic 802 of an exemplary dashboard for monitoring headaches in a subject, in accordance with some embodiments of the present invention. Reference is also made to FIG. 9, is a schematic 902 of an exemplary report summarizing headaches, in accordance with some embodiments of the present invention. Reference is also made to FIG. 10, which is a schematic 1002 presenting parameters and/or features for predicting a headache, organized into categories, in accordance with some embodiments of the present invention. Reference is also made to FIG. 11, which is a schematic 1102 of an exemplary dashboard for presenting parameters correlated with a headache of a user, in accordance with some embodiments of the present invention.

System 200 may implement the acts of the method described with reference to FIGS. 1 and 3-11, by processor(s) 202 of a computing device 204 executing code instructions stored in a memory 206 (also referred to as a program store).

Computing device 204 may be implemented as, for example, a client terminal, a server, a group of connected devices, a computing cloud, a virtual machine, a mobile device, a desktop computer, a thin client, and a mobile device (e.g., a Smartphone, a Tablet computer, a laptop computer, a wearable computer, glasses computer, and a watch computer).

Multiple architectures of system 200 based on computing device 204 may be implemented. For example:

Local architecture—Computing device 204 may be implemented as a standalone device (e.g., client terminal, smartphone) that include locally stored code instructions 206A that implement one or more of the acts described with reference to FIGS. 1 and 3-11. The locally stored instructions may be obtained from another server, for example, by downloading the code over the network, and/or loading the code from a portable storage device. In such implementation, ML model(s) 214A and/or code 206A are locally executed by each standalone device. Data from sensor(s) 250 and/or data inputted by the user via a user interface 220 (e.g., GUI on a touch screen of a smartphone) is locally processed and fed into ML model(s) 214A. ML model(s) 214A may be personalized, trained using a personalized training dataset 214B of personalized extracted features 214C obtained from sensor 250 monitoring the user, optionally excluding data of other subjects. The training of the personalized ML model 214A may be done locally by computing device 204. The outcomes may be presented on user interface 220 (e.g., display) for viewing by the user, for example, prediction of onset of headache, triggers to avoid, and adaptations to treatment of the headache.

Centralized architecture—Computing device 204 executing stored code instructions 206A, may be implemented as one or more servers (e.g., network server, web server, a computing cloud, a virtual server) that provides services (e.g., one or more of the acts described with reference to FIGS. 1 and 3-11) to one or more client terminals 208 over a network 210. For example, providing software as a service (SaaS) to the client terminal(s) 208, providing software services accessible using a software interface (e.g., application programming interface (API), software development kit (SDK)), providing an application for local download to the client terminal(s) 208, providing an add-on to a web browser running on client terminal(s) 208, and/or providing functions using a remote access session to the client terminals 208, such as through a web browser executed by client terminal 208 accessing a web sited hosted by computing device 204. In such implementation, ML model(s) 214A and/or code 206A are centrally executed by computing device 204. Each client terminal 208 sends data from sensor(s) 250 and/or data inputted by the respective user via user interface 220 of the respective client terminal, optionally for creating respective extracted features datasets 214C. Computing device 204 may centrally feed each dataset 214C from each client terminal 208 into ML model(s) 214A. Each respective personalized outcome may be provided to the corresponding client terminal 208 for presentation on the corresponding user interface 220 (e.g., display) for viewing by the respective user. ML model(s) 214A may be general, trained using a general training dataset 214B of extracted features 214C obtained from different sensors 250 monitoring multiple different subjects. The training of the general ML model 214A may be done centrally by computing device 204. Personalized outcomes for different users, optionally based on the general ML model trained using data from different subjects, are provided to each user, for example, personalized prediction of onset of headache, personalized triggers to avoid, and personalized adaptations to treatment of the headache.

Mixed architecture—some features of the methods described with reference to FIGS. 1 and 3-11 are performed by computing device 204, and some features are performed by client terminal(s) 208.

Hardware processor(s) 202 of computing device 204 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 202 may include a single processor, or multiple processors (homogenous or heterogeneous) arranged for parallel processing, as clusters and/or as one or more multi core processing devices.

Memory 206 stores code instructions executable by hardware processor(s) 202, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Memory 206 stores code 206A that implements one or more features and/or acts of the method described with reference to FIGS. 1 and 3-11 when executed by hardware processor(s) 202.

Computing device 204 may include a data storage device 214 for storing data, for example, ML model(s) 214A, training dataset(s) 214B for training ML model(s) 214A, and extracted features dataset 214C that stores features extracted from data obtained from sensor(s) 250 for feeding into ML model(s) 214A, as described herein. Data storage device 214 may be implemented as, for example, a memory, a local hard-drive, virtual storage, a removable storage unit, an optical disk, a storage device, and/or as a remote server and/or computing cloud (e.g., accessed using a network connection).

Network 210 may be implemented as, for example, the internet, a local area network, a virtual network, a wireless network, a cellular network, a local bus, a point to point link (e.g., wired), and/or combinations of the aforementioned.

Computing device 204 and/or client terminal(s) 208 and/or server(s) 212 may be in communication with one or more sensor(s) 250 obtain data, such as for predicting headaches, as described herein. Examples of sensor(s) 250 are described herein, for example, with reference to 104. Data obtained from sensor(s) 250 and/or features extracted from the data may be fed into ML model(s) 214A, as described herein.

Computing device 204 may include a network interface 216 for connecting to network 210, for example, one or more of, a network interface card, a wireless interface to connect to a wireless network, a physical interface for connecting to a cable for network connectivity, a virtual interface implemented in software, network communication software providing higher layers of network connectivity, and/or other implementations.

It is noted that in the standalone implementation, network interface 216 is not necessarily required, as computing device 204 includes sensors 250 and/or user interface 220 in a single device that may operate without externally communication with other devices, for example, a smartphone, a kiosk, and a dedicated device.

Computing device 204 may connect using network 210 (or another communication channel, such as through a direct link (e.g., cable, wireless) and/or indirect link (e.g., via an intermediary computing unit such as a server, and/or via a storage device) with one or more of:

Remote server(s) 212, for example, to obtain data about users and/or subjects from a user dataset(s) 212A, for example, nutritional information from a nutrition web site used by the user, and/or sleep information from a sleep web site used by the user, and/or exercise information from an exercise web site used by the user. The data obtained from user dataset(s) 212A and/or features extracted from the data may be fed into ML model(s)A 214A, as described herein.

Client terminal(s) 208, when computing device 204 is implemented as a server remotely providing the features and/or acts described with reference to FIG. 1.

Sensor(s) 250, as described herein.

Computing device 204 and/or client terminal(s) 208 include and/or are in communication with one or more physical user interfaces 220 that include a mechanism for a user to enter data (e.g., enter data that is fed into ML model(s) 214A) and/or view the displayed results (e.g., instructions for adaptation of treatment for a headache), within a GUI. Exemplary user interfaces 220 include, for example, one or more of, a touchscreen, a display, gesture activation devices, a keyboard, a mouse, and voice activated software using speakers and microphone.

Referring now back to FIG. 1, at 102, the processor accesses and/or trains one or more machine learning models. An exemplary approach for training the ML model is described, for example, with reference to FIG. 3.

The ML model may be a general model, trained on training dataset of records that include parameters obtained from multiple sample individuals. A record includes one or more of: sample physiological, behavioral, and environmental parameters, of a sample individual, and a ground truth label indicative of a state of a headache of the sample individual.

Alternatively, the ML model may be a personalized model, trained on a personalized training dataset of personalized records of the subject that include historical parameters of the subject and a ground truth label indicative of the state of the headache of the subject at a historical time corresponding to the time interval during which the historical parameters were obtained. The personalized training dataset may exclude records of other subjects.

The ML model may be a combined ML model trained on a combined training dataset of records that include data from both the subject and sample individuals.

The ML model may be specific to a type of headache, for example, migraine, or cluster headache, according to the type of headache included in the ground truth of the records. Alternatively, the ML model may be general to migraine and cluster headaches, including records with ground truth labels of both migraine and cluster headaches.

The ML model may be specific to whether the user is currently experiencing a headache (e.g., for reducing the pain of the headache and/or stopping the headache), or whether the user is not currently experiencing a headache (e.g., for preventing onset of the headache and/or for reducing pain intensity of a future headache), according to the ground truth of the records. Alternatively, the ML model may be general to the state of the headache, including records with ground truth labels of both no headache and headache is present.

At 104, the processor accesses data obtained from one or more sensors monitoring the subject. The data may be raw data, such as measurements performed by the sensors.

The sensors may be, for example, wearable sensors such as a watch and/or heart rate sensor, and/or remotely monitoring sensors such as a camera capturing images of the user while sleeping.

Examples of sensors include: a location sensor that outputs location, a motion sensor that outputs motion, heart rate sensor that outputs heart rate, $SPO_2$ level sensor that measures $SPO_2$ levels, respiration rate sensor that outputs respiration rate, an electrode sensor that outputs electro dermal activity, an activity sensor that outputs activity data, a sleep sensor that outputs sleep data.

The sensors may be, for example, an interface (e.g., a graphical user interface presented on a display such as a touch screen of a mobile device) designed to enable a user to enter data, such as pain intensity of a current headache, what food they ate at a current meal, and/or exercise routine.

The data may be obtained, for example, continuously (e.g., throughout the day), at defined intervals (e.g., every 6 hours, or 3 hours, or 1 hour, or 15 minutes, or 1 minute), and/or at set events (e.g., allowing the user to enter the data when they wish and/or by prompting the user to enter data).

At 106, features are extracted from one or more data obtained from sensors, for example, from individual data obtained from individual sensors, and/or from a combination of data obtained from different sensors.

The features may be computed by applying functions to the data, for example, computing heart rate variability, maximum heart rate, and minimum heart rate, from a dataset of multiple heart rate measurements obtained while the subject was sleeping. The features may include the raw data itself, optionally after processing such as to remove noise, for example, body temperature measured by a thermometer within a wearable smartwatch.

The features may be individual features, for example, body temperature, and/or heart rate. The features may be a time sequence, for example, body temperature and/or heart rate measurements every 10 minute over a 6 hour time interval during the night when the subject is sleeping.

Optionally, the features include one or more of: physiological, behavioral and environmental parameters. Other features that do not necessarily fall into the categories of physiological, behavioral, and environmental, may be used. The parameters are fed into the machine learning model, as described herein.

Physiological features represent characteristics of the body of the subject. Examples of physiological parameters, and examples of sensors from which data used to extract the features as physiological parameters include: location of the subject obtained from a location sensor, motion of the subject obtained from a motion sensor, heart rate and/or heart rate variability (HRV) obtained from a heart rate sensor, $SPO_2$ level obtained from an sensor that measures $SPO_2$ levels, respiration rate obtained from a respiration rate sensor, electro dermal activity obtained from an electrode sensor, activity data obtained from an activity sensor, and sleep data obtained from a sleep sensor. The physiological parameters may include computed metrics returned by the sensor including sleeping metrics, and/or sleep recovery (e.g., indicating how much the body recovered during sleep, indicating a goodness of sleep).

Behavioral parameters represent actions performed by the subject. Examples of behavioral parameter(s) include: attendance at work and/or school, involvement of the subject (e.g., work, school, home, social meeting), social meetings (i.e., not at home, school, work), being active, exercise, hobbies, sending messages (e.g., email, instant messages, text messages), and talking on a phone. Behavioral parameters may be measured, for example by one or more of: analysis of location data obtained from a location sensor which may be installed in a smartphone of the user (e.g., global positioning sensor (GPS)), analysis of emails and/or message sent by the user via the smartphone and/or another computing device, analysis of usage of the phone for speaking, and/or analysis of web sites accessed by the user for planning exercises, hobbies, scheduling, and meetings.

Environmental parameters are external to the body of the subject. Examples of environmental parameters, and examples of environmental sensors from which data used to extracted the features as environmental parameters include: ambient temperature obtained from a thermometer, air pressure obtained from a pressure sensor, light intensity obtained from a light intensity sensor, noise intensity obtained from a noise intensity sensor.

Exemplary parameters include:

Movement during the night, for example, number of steps the user took as measured by a pedometer which may be worn as a watch, tossing and turning in bed which may be measured by analyzing images captured by a camera such as of a smartphone.

$SPO_2$ peaks which may be measured by analyzing $SPO_2$ measurements obtained by an $SPO_2$ sensor.

Changes in heart rate during the night (e.g., peak to trough, peak to peak, and the like) which may be measured by analyzing heart rate measurements obtained during the night.

Sleeping segment lengths indicating how long the user slept each time between waking events, in contrast to total sleeping time, which may be measured for example, by analyzing images captured by a camera such as of a smartphone, analyzing EEG measurements, and/or having the user touch a screen when they wake up.

An exemplary combination of parameters includes one or more of the following, optionally all of the following, in combination: sum of calories burned, heart rate variability metric (e.g., mean), heart rate metric (e.g., max), sleep recover score, number of steps, movement during the night of the subject (e.g., steps), oxygen saturation ($SPO_2$) metrics (e.g., $SPO_2$ peaks, and/or minimum) changes in heart rate during the night, sleeping segment length (in contrast to total sleeping time), mean ambient temperature, and median barometric pressure.

Optionally, the parameters include scores of fields of a standardized evaluation tool indicative of pain and/or disability. For example, MIDAS, VAS, KIP Scale, HIT-6, MSQ, and the like. Values of the fields may be features estimated from an analysis of one or more measurements obtained from one or more sensors. The sensor data is mapped to values of the fields of the tools, for example, by a mapping dataset, a trained mapping machine learning model trained on a training dataset of sensor data and corresponding ground truth of scores of the tool(s), and the like.

For example, one or more of the following (which may be used as parameters on their own and/or in other combinations):

Location—The places where the subject usually spends the specific time of day at, obtained for example from an analysis of a schedule application of the user and/or analysis of a location sensor within a mobile device carried by the user.

Motion data, such as type of motion—moving vs. static, lying in bed vs. being active. Amount of activity, such as and that vs. being hectic. Motion data may be obtained, for example, from an analysis of location data obtained from a location sensor and/or analysis of images of the user captured by an imaging sensor.

Migraine annotations—The data the user supplies when having an attack (e.g., via a GUI presented on a display of a device), for example, pain intensity, disabilities that were felt during the attack and mediations that were used.

Communication—The effect of migraine on communications that user has with the environment, by estimating the number of messages exchanged (e.g., in mail, SMS, and applications) and phone calls durations.

Table 1 below indicates an example of mapping sensor source data to disability groups:

| Disability group | Source | | | |
| --- | --- | --- | --- | --- |
| | Location | Motion analysis | Communication | Migraine annotations |
| School or work days | M | M, R | | R |
| Household activity | M | M, R | M, R | R |
| Family, social or leisure activities | | R | M, R | R |
| Medication and pain scale, staying in bed | | + | | + |

Where (M) denotes missed days, (R) denotes reduced activity, and (+) denotes estimated values.

Parameters may be obtained by being fetched from other data resources, for example, online data servers and/or public databases.

When the subject is currently experiencing a headache, the parameters may include an indication of the severity and/or disability of pain due to the headache. The indication of severity and/or disability of pair due to the headache may be obtained, for example, entered by the subject via a user interface (e.g., presenting a GUI on a touchscreen of a mobile device and asking the user to answer questions and/or enter scores), and/or computed from other physiological parameters.

As used herein, the term "ML model" refers to a "headache ML model" which generates the outcome of prediction of the state of the headache, as described herein. The pain ML model is different from the headache ML model.

Parameters may be obtained by feeding data into a pain ML model. When the subject is currently experiencing a headache, a subset of the physiological parameters may be fed into the pain ML model for obtaining an indication of the severity of pain of the headache. The pain ML model may provide a more objective measurement of the severity of pain using objective measures such as heart rate and/or body temperature, for example, in comparison to asking the user to subjectively rank their pain. The pain machine learning model may be trained on a pain training dataset of pain records obtained using historical data of the subject and/or using data from other subjects. A pain record may include a sample subset of parameters of the sample individual and/or subject and a ground truth label indicating pain, for example, using a clinically accepted validated tool.

Alternatively, when the subject is not currently experiencing a headache, a subset of the physiological parameters may be into the pain machine learning model. An indication of predicted a severity of pain for a predicted headache is obtained as an outcome of the pain machine learning model.

The parameters (i.e., the term parameters as used herein) may include an indication of administered treatment. For example, the user took an analgesic of a certain type and a certain dose in an attempt to reduce the pain intensity of a current headache and/or of a predicted headache. The indication of administered treatment is fed into the machine learning model in combination with the physiological, behavioral, and/or environmental parameters, as described herein.

There may be different pain ML models, for example, one pain ML model for subjects currently experiencing the headache, and another pain ML model for subjects that are not currently experiencing the headache. Alternatively, a common ML is used for both cases of currently experiencing the headache and not currently experiencing the headache.

The indication of the severity of pain obtained from the pain ML model is fed as a parameter into the headache ML model.

Exemplary architectures of the pain ML model include, for example, a binary classifier, a multi-class classifier, one or more neural networks of various architectures (e.g., convolutional, fully connected, deep, encoder-decoder, recurrent, graph, combination of multiple architectures), support vector machines (SVM), logistic regression, k-nearest neighbor, decision trees, boosting, random forest, a regressor and the like.

Optionally, features are computing by aggregating data collected over a time interval, for example, computing the average, mean, maximum, minimum, or other aggregation of values over the time interval. The time interval may be, for example, about 5 minutes, 30 minutes, 60 minutes, 3 hours, 6 hours, or other values.

Alternatively or additionally, data imputation is done as new features using one or more of the following exemplary approaches depending on the type of data: last known value (e.g., HRV, HR, SPO2), interpolation methods (e.g., HR, steps, sleeping time, calories burned) and for some variables, imputing the interval proportion by time (e.g., distance walked, calories burned).

At 108, the processor may synchronize the physiological parameters, behavioral parameters, environmental parameters, and/or other parameters described herein. The synchronization may be performed by selecting the different parameters that fall within a common time interval. For example, measurements of sensors used to compute the parameters falling within a common half hour time interval are synchronized together and fed into the ML model together).

The processor may normalize the parameters.

The processor might use additional statistics.

Synchronization may be done in time, using metrics that are time oriented. For example, heart rate measurements collected between 14:15-14:30 are synchronized with $SPO_2$ values collected during between 14:15-14:30.

Static data may be synchronized with the relevant data slice and/or including data that is common to several data slices, for example, temperature, previous night sleeping score, and physical activity (e.g., distance walked/run, fitness time).

The synchronized parameters are fed into the machine learning model, as described herein.

At 110, the processor feeds the parameters into the headache machine learning model. The multiple parameters may be synchronized, as described herein. The multiple parameters may be fed, for example, as a long vector by appending the different parameters, as a two dimensional matrix (e.g., where each row is a different parameter), and/or substantially simultaneously into different inputs of the ML model where each input is designed for a different parameter.

At 112, the processor accesses the prediction of the headache for the subject, which is obtained as an outcome of the machine learning model.

In the case of the subject not having the headache at a time interval during which the physiological parameters are obtained, the prediction of the headache may include a prediction of onset of the headache in the near future, for example, in the next 30 minutes, or 1 hour, or 4 hours, or 6 hours, or 12 hours, or day, or other time intervals.

Optionally, the prediction of the headache includes an estimation of the predicted pain level for the current headache (e.g., how bad the headache will become) and/or for the predicted future headache. The predicted pain may be on a pain scale and/or other standardized tool, for example, on a disability scale indicating amount of disability the user is predicted to incur, and/or on a scale of 1-10 indicating severity of the pain.

Optionally, the prediction of the headache includes an estimated time interval of onset of the predicted headache and/or when a current headache is likely to reach the predicted pain level (e.g., maximum pain, pain level above a threshold indicating disability). For example, imminent, in next hour, in about 2-4 hours, in about 6 hours, in about 12 hours, in about a day, and the like.

Optionally, the prediction of the headache includes multiple scores of fields of a standardized evaluation tool indicative of pain and/or disability due to the headache. For example, MIDAS, VAS, KIP Scale, HIT-6, MSQ, and the like.

When the indication of administered treatment is fed into the machine learning model in combination with the physiological, behavioral and environmental parameters, the outcome of the prediction of the headache may include instructions for administration of a treatment for preventing onset of the headache (when the subject is not currently experiencing the headache), a prediction of an adaptation of the treatment for preventing onset of the headache (when the subject is not currently experiencing the headache), and instructions for administration of a treatment and/or adaptation of the treatment for reduction of severity of the headache (when the subject is currently experiencing the headache). The instructions for administration of treatment may include one or a combination of treatments, for example, medications, alternative therapies, nutrition, diet, sleep, stress reduction, exercise, and the like, as described herein in additional detail. The adaptation of treatment may include one or more of: a recommendation for replacing approved drugs and/or drug combinations between treatments, effectiveness of medication, a change in dose of the medication, a change in frequency of administration of the medication, physical activity, and change in nutrition and/or diet. The adaptation may be selected as being likely to further reduce intensity of pain in comparison to a current treatment, likely to reduce side effects in comparison to the current treatment, and/or likely to prevent future pain.

The treatment and/or adaptation of treatment may be selected for reducing pain of the headache, for example, from a predicted pain that leads to disability (e.g., user unable to work and/or unable to perform basic activities of daily living) to non-disability (e.g., user able to work and/or able to perform basic activities of daily living). In some cases the pain may be eliminated or prevented entirely. In other cases, the pain level is not entirely eliminated but reduced to enable the user to function, by avoiding a state of disability.

The outcome may be provided, for example, presented on a user interface (e.g., text, animation, image, and/or video presented on a display, and/or audio played on speakers), forwarded to another executing process, forwarded to a remote computing device, and/or stored on a data storage device.

The outcome may be presented within a GUI, such as a dashboard, mobile device or printed report. The dashboard may present historical data and/or predicted outcomes, for example, where the headache usually begins, time of day of onset of the headache, and/or aggregated statistics of headache attacks.

At 114, the processor may apply a machine learning model interpretability process for computing relative contribution of the parameters fed into the ML model towards the outcome generated by the ML model. Alternatively or additionally, correlations may be computed between the different features and/or combinations thereof and indication of headaches (e.g., attack events), for example, using statistical tests such as t-tests and/or $X^2$ tests.

The processor may select one or more most contributing parameters, for example, the top-ranked parameters and/or parameters having statistical power above a contribution threshold. The selected contributing parameters may indicate personalized triggers for the headaches of the user. Reducing or avoiding the triggers may reduce or prevent headaches for the user.

The relative contribution of the parameters may be for a specific onset of headache, such as the current headache and/or imminent predicted headache. By adapting and/or eliminating the factors leading to the parameters, the user may reduce the pain of the current headache, stop the current headache, reduce the pain of the predicted headache, and/or prevent the predicted headache. For example, a user may use the interpretability model to discover that the meal she is about to eat, which includes foods high in carbohydrates followed by planning to go to sleep too late and sleeping less than 6 hours is predicted to trigger a migraine the next morning that will cause her to miss work or be unproductive at work. The user may adjust her eating plan by planning to eat healthier earlier in the day, and planning to go to sleep an hour earlier to get 7 or more hours of sleep. By adjusting the meal and sleep schedule, the user is able to avoid triggering the migraine the next morning, enabling the user to work productively the next day.

Exemplary interpretability models for applying to the ML model include: t-tests, $x^2$ test, Shapley values, SHAP (Shapley additive explanations), saliency maps, local surrogate (LIME) and the like.

The identified most contributing parameters may be provided, for example, presented on the display (e.g., within the GUI), fed into another process, provided to a remote computing device, and/or stored on the data storage device.

The identified most contributing parameters may represent a personalized pain signature for the user.

At 116, in response to the prediction of the headache, the subject may be treated for preventing a future headache, reducing pain intensity of the future headache, stopping a current headache, and/or reducing pain intensity of the current headache. The subject may be administered a treatment effective for the headache and/or the administration of the treatment may be adapted.

Exemplary treatments include: NSAID (non-steroidal anti-inflammatory), acetaminophen, aspirin, triptans, etoprolol, propranolol, amitriptyline, divalproex, topiramate, or erenumab-aooe, tricyclic antidepressants, cognitive behavior therapy, biofeedback, massage, acupuncture, exercise routine, sleep therapy, stress reduction therapy, and change in diet.

Instructions for administration of the treatment may be presented on the user interface, for example, a message, image, animation and/or video presented on a display and/or an audio message played on speakers.

At 118, the processor may dynamically update the machine learning model. The processor may dynamically create a new record using new values of the parameters that were fed into the ML model and a new value(s) for the ground truth label corresponding to the new values of the parameters generated by the ML model. The new record may be adjusted, for example, based on new data, such as the user correcting values of the new record. The ML model may be updated using the new record.

At 120, one or more features described with reference to 104-118 are iterated, for example, continuously (e.g., throughout the day), at defined intervals (e.g., every 6 hours, or 3 hours, or 1 hour, or 15 minutes, or 1 minute), and/or selected events (e.g., allowing the user to enter a trigger when they wish to obtain the prediction of the headache). The features may be iterated, for example, to provide the user with monitoring for predicted headaches, monitoring for triggers, and/or monitoring for administration of treatments and/or adaptation of treatment. The monitoring may be, for example, continuous, at the defined intervals, and/or at the selected events.

The iterations may enable prediction of specific headache events, optionally per headache event. Triggering of the specific headache events may be avoided, and/or the experienced pain may be reduced (e.g., to prevent disability, such as allowing the user to have a productive day).

The iterations that include administration of treatment and reaction of the subject to the treatment may be performed for optimizing treatment of the subject, for example, when to administer the treatment(s), dosage of treatment(s), frequency of the treatment(s), and/or changes of the treatment(s). The optimization may be define within clinical guidelines and/or best practices, such as FDA and/or CE. The initial dosage and/or frequency may be as defined by the clinical guidelines.

Referring now back to FIG. 3, at 302, the processor accesses data obtained from multiple sensors monitoring the subject and/or the sample individual is obtained, for example, as described with reference to 104 of FIG. 1.

At 304, the processor extracts features from the data. The features include parameters, which are fed into the ML model. For example, as described with reference to 106 of FIG. 1.

At 306, the processor accesses an indication of the state of the headache of the subject and/or sample individual, serving as ground truth. The indication of the state of the headache may be obtained by a manual user input, for example, into a user interface of a mobile device, such as a GUI presented on a touchscreen. The manual user input may be indicative of at least one of: when the headache started, when the headache ended, pain level of the headache, disability caused by headache.

At 308, the processor accesses an indication of administered treatment. The processor may access, for example, the treatment that was administered, the time of administration, the dose, and the effect of the administration of the treatment in reducing pain intensity of the headache. The indication of administered treatment may be obtained, for example, by manual user input, extracted from a medical record (e.g., physician prescription) and the like.

At 310, the features (i.e., parameter) are synchronized, optionally with the ground truth. For example, as described with reference to 108 of FIG. 1.

At 312, the processor creates a record. The record includes the sample parameters of the sample individual and/or subject (obtained as described with reference to 304) and the ground truth label indicative of the state of the headache of the sample individual and/or subject (obtained as described with reference to 306), optionally synchronized (created as described with reference to 310). The ground truth may include sample scores of fields of one or more standardized headache evaluation tools, as described herein. The scores may be provided, for example, manually entered by the users. The record may include an indication of treatment administered to the sample individual and/or the ground truth may include an indication of the adaptation of the treatment.

At 314, the processor creates a training dataset of multiple records of multiple sample individuals and/or of the subject (e.g., personalized training dataset), by iterating features described with reference to 302-312. The personalized training dataset may include records of the subject and exclude records of other sample individuals.

At 316, the machine learning model is trained on the training dataset(s). The prediction of the headache for the subject is obtained as an outcome of the machine learning model in response to an input of physiological parameters obtained from data outputted by sensors monitoring the subject, for example, as described with reference to FIG. 1.

Optionally, the machine learning model is implemented based on a reinforcement learning approach, for example, Q learning.

The reinforcement learning approach may be defined as follows: an action taken by the subject is the administration of a targeted treatment for a current state of the headache. The current state may be, for example, one or more of: presence or absence of the headache, type of headache (e.g., migraine, cluster), and intensity of pain of the headache. The treatment may be the set of possible treatments for the type of headache, for example, as described herein and/or based on clinical guidelines. A next state (or new state) is the prediction of the headache in response to the administered treatment, optionally the probability of moving to each possible state given the current state and the administered treatment. A reward is a decrease in pain and/or frequency of the headache, and/or prevention of the headache. Reinforcement learning may be used for filing optimal (or near optimal) treatment policy for the subject. During the exploration phase, the lower and/or upper dosages and/or frequency of administration may remain within clinical guidelines, such as FDA/CE and/or manufacturer recommendations.

The ML model may be implemented using other architectures, for example, a binary classifier (e.g., headache likely or not likely), a multi-class classifier (e.g., prediction of when the headache will occur and/or predicted pain intensity), linear discriminant analysis (LDA), one or more neural networks of various architectures (e.g., convolutional, fully connected, deep, encoder-decoder, recurrent, graph, combination of multiple architectures), support vector machines (SVM), logistic regression, k-nearest neighbor, decision trees, boosting, random forest, a regressor and the like.

The ML model is provided, for example, stored on a data storage device, forwarded to a remote computing device, and/or executed by the processor.

At 318, the ML model may be updated with one or more new records, for example, as described with reference to 118 of FIG. 1.

Referring now back to FIG. 4, the features described with reference to FIG. 4 may be implemented as, be based on, be combined with, and/or be integrated with, one or more features described with reference to FIG. 1 and/or FIG. 3.

At 402, raw data is obtained from sensors, as described herein.

At 404, annotations are assigned to the raw data. The annotations may be provided by a user, for example, manually entered using a user interface. The annotation may include an indication of headache, for example, start time, end time, pain level estimation, disability caused during the attack, treatment (if used), and related data.

At 406, the data is processed, for example, records are created by assigning the annotations as ground truth to the data. The data may be normalized and/or synchronized (e.g., between sensors). Missing data may be handled.

At 408, features are extracted from the data, as described herein.

At 410, the data may be split into training data and testing data sets. The data split for training/validation/testing may be done as sequences rather than discrete points according to data blocks (e.g., day, night (defined by sleeping time), special activity (e.g. walking, running, swimming, etc.), and time sequence that can be measured in hours or days. etc.). The split helps to ensure that the data blocks are not dependent on data information which may prevents information leaks.

At 412, one or more ML models are trained on the training dataset.

At 414, a certain ML model may be selected for the subject to be used for predicting headaches.

At 416, the ML model selected for each subject is fed the data collected from the sensors monitoring the subject. The prediction of headache is provided, for example, presented on a display.

At 418, the processor may perform an a posteriori performance of the ML model. The performance data may be used for future model training and/or optimization.

Referring now back to FIG. 5, architecture 500 may include features and/or components described with reference to FIGS. 1-4.

Architecture 500 may include an application service 502 for synchronizing with an application which may run, for example, on a mobile device, and/or other client, a data pipeline service 504 for generating different data, and an artificial intelligence service for training ML models and/or inference by the ML models.

External fetchers 506 obtain raw data 508, for example, measurements from wearable sensors monitoring the subject and/or other data sources such as sensors monitoring the external environment, databases, and data of behavior of the subject (e.g., diet of the user). The raw data may trigger a new file, for example, a new set of features for training and/or inference. The raw data may be parsed 510 (e.g., organized into time intervals and/or synchronized) and tagged 512 with ground truth labels (e.g., state of headache, intensity of headache, start of headache, end of headache) manually by the user and/or automatically by code. Processed and/or tagged data 514 is used for training 516 for generating ML models 518. The trained models generate predictions 520 of headaches for the subject, for example, based on a schedule, in response to user request, and/or continuously. The predictions may be stored in an aggregated data repository 522.

Tagged data 512 may be obtained from an application server 524 by synchronizing data entered via an application 526 running on a mobile device of a user, for example, a smartphone and/or smartwatch. Data collected by application server 524 may under an extraction, transformation, and loading (ETL) process 528 for storage in aggregated data repository 522.

Processed and/or tagged data 514 may be processed by different data aggregation processes 530. Processed and/or tagged data 514 may be analyzed for generating insights 532, for example, most significant features that contribute towards a headache. The aggregated data and/or features may be stored in aggregated data repository 522.

Additional data may be fed into aggregated repository 522, for example, data collected by a server 534, data entered by a user and/or collected by an application 536 running on a mobile device, and/or data from other external sources such as health data of the use via the FHIR (Fast Healthcare Interoperability Resources) standard 538.

Data in aggregated repository 522 may be used, for example, for viewing by a user (e.g., to see discovered triggers affecting their headache, history of headaches and improvements in headaches), updating of ML models, analysis by healthcare professionals, and the like.

Referring now back to FIG. 6, plot 602 graphically depicts a plot of personalized physiological metrics of a user, indicating normalized personalized risk factors for a headache for the user based on the machine learning model. For example, for the user, ANS, respiratory, and cardiovascular parameters are most likely to be risk factors for triggering migraines. Sleep parameters are less likely to trigger migraine. Movement parameters are unlikely to trigger migraine. The plot may indicate a migraine signature, and/or a pain signature. Values of the plot may be used for computing similarity scores to create clusters of similar users, for example, for generating different training datasets for the different clusters of users.

Referring now back to FIG. 7, graph 702 indicates stages of migraine as manifested by a user, in accordance with some embodiments of the present invention. Examples of stages include normal 704, prodrome 706, during event 708, and postdrome 710.

Various embodiments and aspects of the present invention as delineated hereinabove and as claimed in the claims section below find experimental support in the following example.

Referring now back to FIG. 8, dashboard 802 may present a summary of headaches of the subject over a historical time interval, and/or provide data for each headache event. A summary of parameters that are the largest contributors to the headache predicted by the ML model may be presented, for example, under the headings Pain 804, Biomarkers 806, and Activity 808. For example, under the heading Pain, average Pain Duration is presented. Under the heading Biomarkers, the actual sleep versus recommended sleep is presented. Under the heading Activity heading, the number of steps taken versus recommended or average steps taken may be presented. Details of the parameters that are summarized may be provided for each headache event 810. A summary and details of when medications were taken, and the like, may be presented.

Referring now back to FIG. 9, report 902 may be for a specific user. Report 902 may summarizes, for example, number of days with pain, how long each attack lasted, locations where the attack occurred, when during the day and/or week attacks occurred, and generated recommendations for reducing attacks based on identified parameters that most contributed to the prediction of headache by the ML model, as described herein.

Referring now back to FIG. 10, schematic 1002 visually presents parameters and/or features for predicting a headache, organized into categories, as described herein.

Referring now back to FIG. 11, dashboard 1102 may be used, for example, by a physician for evaluating triggers of the headache. Dashboard 1102 may include a title section 1104 indicating when the subject last visited the physician, and prescribed medications. A summary section 1106 may summarize multiple headaches over a historical time interval (e.g., last 4 weeks), for example, average sleep per night, average attack duration, and others as shows. A correlation section 1108 presents parameters found to correlate with headache, for example, by the interpretability model(s) as described herein. For example, geographic location, hours of sleep, humidity, noise, time of week, and time of day. The physician may analyze correlations 1108 to help recommend changes to the subject that are likely to reduce headaches, for example, increase sleep, avoid high noise, and/or to take medication in the evening.

EXAMPLES

Reference is now made to the following example, which together with the above descriptions illustrate some embodiments of the invention in a non limiting fashion.

Inventors performed an experiment on subjects to predict headaches, based on embodiments described herein. Testing was conducted on a cohort of users. Users used various smart devices and advanced cellular phones. All users were previously diagnosed with chronic migraine or cluster headache. Features were computed from outputs of sensors monitoring subjects. The features were fed into a trained machine learning model, to obtain predictions of headaches. A confusion matrix of the results (aggregated to day-level) is presented below in Table 2.

TABLE 2

|  | precision | recall | f1-score | support |
|---|---|---|---|---|
| 0.0 | 0.86 | 1.00 | 0.92 | 6 |
| 1.0 | 1.00 | 0.75 | 0.86 | 4 |
| accuracy |  |  | 0.90 | 10 |
| macro avg | 0.93 | 0.88 | 0.89 | 10 |
| weighted avg | 0.91 | 0.90 | 0.90 | 10 |
| [[6 0] |  |  |  |  |
| [1 3]] |  |  |  |  |

The confusion matrix of Table 2 provides empirical evidence that headaches are predictable in subjects using embodiments described herein.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant machine learning models will be developed and the scope of the term machine learning model is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer implemented method for predicting a headache for a subject that is implemented by a machine learning model executing on the computer, comprising:
   receiving, by the machine learning model, a plurality of physiological, behavioral, and environmental parameters obtained from a plurality of sensors monitoring the subject;
   obtaining, by the machine learning model, an indication of administered treatment in combination with the plurality of physiological, behavioral and environmental parameters;
   extracting, by the computer, features from the plurality of sensors monitoring the subject;
   time-synchronizing, by the computer, the features extracted from the plurality of sensors monitoring the subject;
   receiving, by the machine learning model, the time-synchronized features in combination with the plurality of physiological, behavioral and environmental parameters;
   wherein the time-synchronizing may be performed by selecting different parameters that fall within a common time interval and feeding the parameters as vectors in the machine-learning model; and
   developing, by the computer based on the machine learning model, the prediction of the headache for the subject;
   wherein the machine learning model is a trained machine learning model, wherein training the machine learning model further comprises:
   training the machine learning model on a first training dataset comprised of a first plurality of records wherein each record of the first plurality is developed for a respective one of sample individuals, wherein each record of the first plurality includes a plurality physiological, behavioral, and environmental parameters that are collected for the respective one of the sample individuals to which it pertains and a ground truth label indicative of a state of a headache of the respective one of the sample individuals, to which it pertains; and
   further training the machine learning model on a second training dataset comprised of a second plurality of records that are personalized records of the subject, wherein each personalized record of the second plurality of records includes a plurality of historical physiological, behavioral, and environmental parameters of the subject and a ground truth label indicative of the state of headache of the subject corresponding to a time of collection of the historical physiological, behavioral, and environmental parameters of the subject for each respective personalized record of the second plurality;
   wherein the prediction of the headache further includes a prediction of an adaptation of the treatment for preventing onset of the headache when the subject is not currently experiencing a headache or for reduction of severity of the headache currently experienced by the subject.

2. The computer implemented method of claim 1, wherein the plurality of physiological, behavioral, and environmental parameters are a combination of one or more of the following: sum of calories burned, mean heart rate variability, maximum heart rate, sleep recover score, number of steps, movement during a night of the subject, peak and/or minimum oxygen saturation, changes in heart rate during the night, sleeping segment length, mean ambient temperature, and median barometric pressure.

3. The computer implemented method of claim 1, wherein the plurality of physiological parameters are selected from a group consisting of: movement during a night, $SPO_2$ peaks, changes in heart rate during the night, and sleeping segment lengths indicating how long the subject slept each time between waking events.

4. The computer implemented method of claim 1, wherein at least one of the plurality of physiological, behavioral, and environmental parameters comprises a time sequence of a plurality of measurements obtained over a time interval.

5. The computer implemented method of claim 1, wherein a type of the predicted headache is one of a group comprising migraine and cluster headache.

6. The computer implemented method of claim 1, further comprising: in response to the prediction of the headache, treating the subject for the headache by administering a treatment effective for the headache.

7. The computer implemented method of claim 6, wherein the treatment effective for the headache is selected from a group comprising: non-steroidal anti-inflammatory (NSAID), acetaminophen, aspirin, triptans, etoprolol, propranolol, amitriptyline, divalproex, topiramate, or erenumab-aooe, tricyclic antidepressants, cognitive behavior therapy, biofeedback, massage, acupuncture, exercise, sleep therapy, stress reduction therapy, and change in diet.

8. The computer implemented method of claim 1, wherein the prediction of the headache comprises a plurality of scores of a plurality of fields of a standardized evaluation tool indicative of pain and/or disability due to the headache, wherein each record of the first plurality and each record of the second includes ground truth labels indicative of sample scores for the plurality of fields of the standardized evaluation tool.

9. The computer implemented method of claim 1, wherein the plurality of physiological parameters obtained from the plurality of sensors are selected from a group comprising: location of the subject obtained from a location sensor, motion of the subject obtained from a motion sensor, heart rate or HRV obtained from a heart rate sensor, $SPO_2$ level obtained from an sensor that measures $SPO_2$ level, respiration rate obtained from a respiration rate sensor, electro dermal activity obtained from an electrode sensor, activity data obtained from an activity sensor, sleep data obtained from a sleep sensor, or computed metrics returned by the sensor including sleeping metrics, and sleep recovery.

10. The computer implemented method of claim 1, wherein the indication of the state of each headache is obtained by receiving a manual user input into a user interface of a mobile device, the manual user input indicative of at least one of: when headache started, when headache ended, pain level of the headache, disability caused by headache, and treatment taken by the subject.

11. The computer implemented method of claim 1, wherein the behavioral parameters are selected from a group comprising: attendance, involvement, social meetings, exercise, hobbies, sending messages, and talking on a phone.

12. The computer implemented method of claim 1, wherein the environmental parameters and at least one environmental sensor from which the environmental parameters are defined is selected from a group comprising: temperature obtained from a thermometer, pressure obtained from a pressure sensor, light intensity obtained from a light intensity sensor, noise intensity obtained from a noise intensity sensor, and fetched from other data resources.

13. The computer implemented method of claim 1, wherein the prediction of the headache comprises prediction of onset of the headache when the subject does not have the headache at a time interval during which the plurality of physiological parameters are obtained.

14. The computer implemented method of claim 1, wherein the adaptation of the treatment includes at least one of: a recommendation to replace approved drugs and/or drug combinations between treatments, effectiveness of medication, a change in dose of the medication, a change in frequency of administration of the medication, physical activity, change in nutrition and/or diet, wherein the adaptation is for at least one of: likely to further reduce intensity of pain in comparison to a current treatment, and likely to reduce side effects in comparison to the current treatment.

15. The computer implemented method of claim 1, further comprising treating the subject by administration of the adaptation of the treatment.

16. The computer implemented method of claim 1, wherein when the subject is currently experiencing a headache, the plurality of physiological, behavioral and environmental parameters includes an indication of the severity and disability of pain due to the headache, obtained by at least one of: received from the subject via a user interface, and computed from other physiological parameters, wherein the adaptation of the treatment is for reducing the severity of the pain or prevention of the pain.

17. The computer implemented method of claim 1, when the subject is currently experiencing a headache, further comprising:
  receiving, by a pain machine learning model, a subset of the plurality of physiological parameters;
  developing, by a pain machine learning model, an indication of the severity of pain of the headache,
  wherein the pain machine learning model is trained on a pain training dataset of a plurality of pain records, wherein a pain record includes a sample subset of plurality of physiological, behavioral and environmental parameters of a sample individual and/or of the subject and a ground truth label indicating pain,
  wherein the indication of the severity of pain is supplied by the pain machine learning model to the machine learning model, wherein the prediction of the headache further comprises instructions for treatment for preventing of pain or reducing severity of pain of the current headache.

18. The computer implemented method of claim 1, when the subject is not currently experiencing a headache, further comprising:
  receiving, by a pain machine learning model, a subset of the plurality of physiological parameters;
  developing, by a pain machine learning model, an indication of the severity of pain of the headache,
  wherein the pain machine learning model is trained on a pain training dataset of a plurality of pain records, wherein a pain record includes a sample subsets of plurality of physiological parameters of a sample subject and a ground truth label indicating pain,
  wherein the indication of the severity of pain is supplied by the pain machine learning model to the machine learning model, wherein the prediction of the headache further comprises instructions for treatment for reducing severity of predicted pain of the predicted headache.

19. The computer implemented method of claim 1, wherein the machine learning model is based on a reinforcement learning approach, where an action taken by the subject is administration of a targeted treatment for a current state of the headache, a next state is the prediction of the headache in response to the administered treatment, and a reward is a decrease in pain of the headache, frequency or preventing the headache.

20. The computer implemented method of claim 1, wherein at least one record of the first plurality of records of the first data set further includes time-synchronized features extracted from a plurality of training sensors monitoring the sample individual to whom the at least one record pertains.

21. The computer implemented method of claim 1, wherein at least one record of the second plurality of records of the second set further includes time-synchronized features extracted from a plurality of sensors monitoring the subject at the time of collection of the historical physiological, behavioral, and environmental parameters of the subject.

22. The computer implemented method of claim 1, further comprising:
supplying, by the computer, based on the trigger, instructions for a course of action to be undertaken by the subject to at least one of prevent and ameliorate the predicted headache.

23. A system for predicting a headache for a subject by a machine learning model that is executing on the system, comprising:
a processing circuitry; and
a memory, the memory containing instructions that, when executed by the processing circuitry, configure the system to:
receive, by the machine learning model, a plurality of physiological, behavioral, and environmental parameters obtained from a plurality of sensors monitoring the subject;
obtain, by the machine learning model, an indication of administered treatment in combination with the plurality of physiological, behavioral and environmental parameters;
extract features from the plurality of sensors monitoring the subject;
time-synchronize the features extracted from the plurality of sensors monitoring the subject;
receive, by the machine learning model, the time-synchronized features in combination with the plurality of physiological, behavioral and environmental parameters;
wherein the time-synchronizing may be performed by selecting different parameters that fall within a common time interval and feeding the parameters as vectors in the machine-learning model; and
develop based on the machine learning model, the prediction of the headache for the subject;
wherein the machine learning model is a trained machine learning model, wherein the system is further configured to train the machine learning model by:
training the machine learning model on a first training dataset comprised of a first plurality of records wherein each record of the first plurality is developed for a respective one of sample individuals, wherein each record of the first plurality includes a plurality physiological, behavioral, and environmental parameters that are collected for the respective one of the sample individuals to which it pertains and a ground truth label indicative of a state of a headache of the respective one of the sample individuals, to which it pertains; and
further training the machine learning model on a second training dataset comprised of a second plurality of records that are personalized records of the subject, wherein each personalized record of the second plurality of records includes a plurality of historical physiological, behavioral, and environmental parameters of the subject and a ground truth label indicative of the state of headache of the subject corresponding to a time of collection of the historical physiological, behavioral, and environmental parameters of the subject for each respective personalized record of the second plurality;
wherein the prediction of the headache further includes a prediction of an adaptation of the treatment for preventing onset of the headache when the subject is not currently experiencing a headache or for reduction of severity of the headache currently experienced by the subject.

* * * * *